(12) United States Patent
Dang et al.

(10) Patent No.: US 10,596,287 B2
(45) Date of Patent: Mar. 24, 2020

(54) APPARATUS AND METHOD TO LINK MEDICAL DEVICE STERILIZATION EQUIPMENT

(71) Applicant: ASP Global Manufacturing GmbH, Schaffhausen (CH)

(72) Inventors: Philippe Kanh Dang, San Diego, CA (US); Venkata Danam, Irvine, CA (US); Yaeer Lev, Redondo Beach, CA (US); Jacob S. Childs, Huntington Beach, CA (US); Darius D. Eghbal, Sierra Madre, CA (US); Jeremy M. Yarwood, Aliso Viejo, CA (US); Brian J. Thompson, Aliso Viejo, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 221 days.

(21) Appl. No.: 15/441,749

(22) Filed: Feb. 24, 2017

(65) Prior Publication Data
US 2017/0252472 A1  Sep. 7, 2017

Related U.S. Application Data

(60) Provisional application No. 62/302,257, filed on Mar. 2, 2016, provisional application No. 62/316,722, filed
(Continued)

(51) Int. Cl.
*A61L 2/24* (2006.01)
*H04W 76/11* (2018.01)
(Continued)

(52) U.S. Cl.
CPC ............ *A61L 2/24* (2013.01); *A61B 1/00006* (2013.01); *A61B 1/00062* (2013.01);
(Continued)

(58) Field of Classification Search
CPC ..... A61L 2/24; A61L 2/14; A61L 2/16; A61L 2/20; A61L 2/04; A61L 2/28;
(Continued)

(56) References Cited

U.S. PATENT DOCUMENTS 6,063,591 A    5/2000  Bolea
6,325,972 B1  12/2001  Jacobs et al.
(Continued)

FOREIGN PATENT DOCUMENTS

EP    1 617 878 A1    1/2006
EP    0 981 641 B1    5/2006
(Continued)

OTHER PUBLICATIONS

Extended European Search Report and Written Opinion dated Aug. 2, 2017 for Application No. EP 17158962.5, 8 pgs.
(Continued)

*Primary Examiner* — Regina M Yoo
(74) *Attorney, Agent, or Firm* — Frost Brown Todd LLC

(57) ABSTRACT

A communication hub provides communication between a number of medical device processing components within a network. A user may access the communication hub via a user device such as a smartphone or computer and monitor and manage configurations and information relating to the medical device processing components. Features include the ability to view current status of medical device processing components in order to identify a device that is available for current use, to receive notifications of failed or completed tasks on devices, to disable or enable devices remotely, to view statistics and data visualizations of the performance and use of devices, and other similar features.

19 Claims, 23 Drawing Sheets

Related U.S. Application Data on Apr. 1, 2016, provisional application No. 62/376,517, filed on Aug. 18, 2016.

(51) Int. Cl.
| | |
|---|---|
| *A61B 1/12* | (2006.01) |
| *G06Q 50/22* | (2018.01) |
| *A61B 1/00* | (2006.01) |
| *A61L 2/04* | (2006.01) |
| *A61L 2/14* | (2006.01) |
| *A61L 2/16* | (2006.01) |
| *A61L 2/20* | (2006.01) |
| *A61L 2/28* | (2006.01) |
| *H04W 68/00* | (2009.01) |
| *H04W 84/12* | (2009.01) |

(52) U.S. Cl.
CPC ............... *A61B 1/123* (2013.01); *A61L 2/04* (2013.01); *A61L 2/14* (2013.01); *A61L 2/16* (2013.01); *A61L 2/20* (2013.01); *A61L 2/28* (2013.01); *G06Q 50/22* (2013.01); *H04W 68/005* (2013.01); *H04W 76/11* (2018.02); *A61B 1/00059* (2013.01); *A61L 2202/14* (2013.01); *A61L 2202/24* (2013.01); *H04W 84/12* (2013.01)

(58) Field of Classification Search
CPC . A61L 2202/24; A61L 2202/14; G06Q 50/22; A61B 1/00062; A61B 1/00006; A61B 1/123; A61B 1/00059; G06F 19/00; H04W 76/11; H04W 68/005
See application file for complete search history.

(56) References Cited

U.S. PATENT DOCUMENTS

| | | | |
|---|---|---|---|
| 6,365,102 B1 | 4/2002 | Wu et al. | |
| 6,447,719 B1 | 9/2002 | Agamohamadi et al. | |
| 6,485,978 B1 | 11/2002 | Kirckof et al. | |
| 6,852,277 B2 | 2/2005 | Platt et al. | |
| 6,852,279 B2 | 2/2005 | Williams et al. | |
| 6,936,434 B2 | 8/2005 | McDonnell et al. | |
| 6,939,519 B2 | 9/2005 | Agamohamadi et al. | |
| 6,986,736 B2 | 1/2006 | Williams et al. | |
| 7,479,257 B2 | 1/2009 | Nguyen et al. | |
| 7,686,761 B2 | 3/2010 | Jackson et al. | |
| 8,246,909 B2 | 8/2012 | Williams et al. | |
| 9,056,147 B2* | 6/2015 | Ma | A61L 2/24 |
| 9,216,440 B2* | 12/2015 | Ma | A61M 39/16 |
| 9,410,180 B2 | 8/2016 | Pederson et al. | |
| 2003/0170901 A1 | 9/2003 | Kippenhan et al. | |
| 2004/0197848 A1 | 10/2004 | Behun et al. | |
| 2013/0323117 A1* | 12/2013 | Ma | A61M 39/16 422/1 |
| 2013/0323120 A1* | 12/2013 | Ma | A61L 2/24 422/24 |
| 2014/0053871 A1* | 2/2014 | Ma | A61M 39/16 134/6 |
| 2017/0252473 A1 | 9/2017 | Thompson et al. | |
| 2017/0252474 A1 | 9/2017 | Thompson et al. | |
| 2017/0253905 A1 | 9/2017 | Eghbal et al. | |

FOREIGN PATENT DOCUMENTS

| | | |
|---|---|---|
| EP | 2 340 853 A1 | 7/2011 |
| EP | 2 792 294 A1 | 10/2014 |
| JP | 2008-200126 A | 9/2008 |
| WO | WO 01/10475 A1 | 2/2001 |
| WO | WO 2004/093925 A1 | 11/2004 |
| WO | WO 2005/048041 A2 | 5/2005 |
| WO | WO 2006/086547 A2 | 8/2006 |
| WO | WO 2013/181393 A1 | 12/2013 |
| WO | WO 2014/159696 A1 | 10/2014 |
| WO | WO 2015/049002 A1 | 4/2015 |
| WO | WO 2015/080777 A1 | 6/2015 |

OTHER PUBLICATIONS

U.S. Appl. No. 15/057,768, filed Mar. 1, 2016.
U.S. Appl. No. 15/157,800, filed May 20, 2016.
U.S. Appl. No. 15/441,707, filed Feb. 24, 2014.
U.S. Appl. No. 15/441,734, filed Feb. 24, 2014.
U.S. Appl. No. 15/441,786, filed Feb. 24, 2014.
U.S. Appl. No. 62/302,257, filed Mar. 2, 2016.
U.S. Appl. No. 62/316,722, filed Apr. 1, 2016.
U.S. Appl. No. 62/376,517, filed Aug. 18, 2016.
European Search Report and Written Opinion, Extended, dated Jul. 27, 2017 for Application No. EP 17158975.7, 9 pgs.
European Search Report and Written Opinion, Partial, dated Aug. 1, 2017 for Application No. EP 17158813.0, 13 pgs.
European Search Report and Written Opinion, Extended, dated Nov. 9, 2017 for Application No. EP 17158813.0, 11 pgs.

\* cited by examiner

Cycle #20, #001, CSSD

STERRAD Cycle Info

| | |
|---|---|
| Cycle Status: | ☑ Completed |
| STERRAD ID: | #001 |
| Cycle #: | 20 |
| Cycle Type: | STANDARD |
| Load Conditioning: | Disabled |
| Operator: | D.Thomas |
| Cycle Date: | 09-Feb-2016 |
| Cycle Start Time: | 12:01 PM |
| Cycle End Time: | 12:55 PM |
| Elapsed Time: | 55 Mins |
| Facility Name: | — |
| Department Name: | CSSD |
| Cassette lot Number: | 123456-01 |
| Biological Indicator: | Processed |
| Cycle Notes: | — |

Test Biological Indicator Info

| | |
|---|---|
| Biological Indicator Result: | ◯ Failed (Positive) Velocity 1 |
| Biological Indicator Reader: | Test |
| Biological Indicator: | |
| Lot Number: | 123456-01 |
| Serial Number: | 987654321 |
| Expiration Date: | 01/20/17 |
| Added By: | J.Smith |
| Time Added: | 01:45 AM |
| Date Added: | 20-Oct-2015 |
| Result Time: | 02:15 PM |
| Chemical Indicator Color Change: | Yes |
| Temperature: | 60°C |

Cycle Summary | Cycle Files

BI-01 STERRAD VELOCITY — Connected — Log | Table

Result Log From 09-Feb-2016 to 11-Feb-2016 — 20 Results — Search Cycle Log

| Start Date & Time | Biological Indicator Type ▼ | Status ▼ | Cycle # | Cycle Type ▼ | Cycle Status ▼ |
|---|---|---|---|---|---|
| 09-Feb-2016 - 09:14PM | Test | Pending... | 20 | STANDARD | ☑ Completed |
| 09-Feb-2016 - 10:15PM | Test | ○ Result in 12 min | 19 | FLEX | ☑ Completed |
| 09-Feb-2016 - 11:20PM | Test | ● Failed (Positive) | 18 | DUO | ☑ Completed |
| 10-Feb-2016 - 12:30AM | Test | ○ Passed (Negative) | 17 | EXPRESS | ☑ Completed |

Test Biological Indicator Info
Start Date/Time: 10-Feb-2016 - 12:30AM
Biological Indicator Result: ○ Passed (Negative)
Added By: J.Smith

STERRAD Cycle Info
STERRAD ID: #001
Cycle Start Date/Time: 10-Feb-2016 - 12:01AM
Cycle Type: EXPRESS
Operator: D.Thomas More Info...

| 10-Feb-2016 - 01:30AM | Control | ○ Passed (Negative) | 16 | STANDARD | ☑ Completed |

Device Management

List of Devices — Search Result Table — Active | All

| Device ID | Device Category | Department | Device Pairing |
|---|---|---|---|
| STERRAD 1 | Sterilizer | Pediatrics | — ✎ |

Serial Number: 10033-123323
Device Model: STERRAD 100NX
Software Version: 981274-34324
Firmware Version: 981274-34324
Cycle Types: STANDARD, DUO, FLEX, EXPRESS Button

| STERRAD 2 | Sterilizer | Urology | — ✎ |
| READER | B.I.Reader | Pediatrics | — ✎ |
| EVOTECH | Endoscope Reprocessor | CSSD | ⊙ ✎ |
| DARWIN | Endoscope Reprocessor | CSSD | ⊙ ✎ |

1098

List of Devices | Add Device

APPARATUS AND METHOD TO LINK MEDICAL DEVICE STERILIZATION EQUIPMENT

PRIORITY

This application claims priority to U.S. Provisional Patent Application No. 62/302,257, entitled "System and Method for Sterilizing Medical Devices," filed Mar. 2, 2016, the disclosure of which is incorporated by reference herein.

This application also claims priority to U.S. Provisional Patent Application No. 62/316,722, entitled "System and Method for Sterilizing Medical Devices," filed Apr. 1, 2016, the disclosure of which is incorporated by reference herein.

This application also claims priority to U.S. Provisional Patent Application No. 62/376,517, entitled "Apparatus and Method to Link Medical Device Sterilization Equipment," filed Aug. 18, 2016, the disclosure of which is incorporated by reference herein.

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, peracetic acid, and vapor phase sterilization, either with or without a gas plasma and ethylene oxide (EtO). Each of these methods may depend to a certain extent on the diffusion rates of the sterilization fluids (e.g., gases) upon or into the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device. Diffusion of the sterilant may be particularly problematic for medical devices that have diffusion-restricted spaces therein because these diffusion-restricted spaces may reduce the likelihood that a sterilization cycle may be effective. For example, some endoscopes have one or more long narrow lumens into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; U.S. Pat. No. 6,447,719, entitled "Power System for Sterilization Systems Employing Low Frequency Plasma," issued Sep. 10, 2002, the disclosure of which is incorporated by reference herein; and U.S. Provisional Pat. App. No. 62/316,722, entitled "System and Method for Sterilizing Medical Devices," filed Apr. 1, 2016, the disclosure of which is incorporated by reference herein.

Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle. The presence or absence of living microorganisms in the biological indicator will indicate whether the sterilization cycle was effective.

In view of the foregoing, it may be desirable to provide a sterilization system that minimizes opportunities for operator error, thereby maximizing the likelihood of successful sterilization cycles, thereby minimizing the risk of patient infection. While a variety of systems and methods have been made and used for medical device sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 17 shows an example of an interface that may be used to view additional information on a medical device processing component's tasks via a user device coupled with the communication hub of FIG. 7 or directly via the communication hub of FIG. 8;

FIG. 26 shows an example of an interface that may be used to view and manage additional information on an indicator analyzer task via a user device coupled with the communication hub of FIG. 7 or directly via the communication hub of FIG. 8;

FIG. 27 shows an example of an interface that may be used to view and manage additional information for a medical device processing component connected to a network via a user device coupled with the communication hub of FIG. 7 or directly via the communication hub of FIG. 8;

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Sterilization System and Devices

A. System Overview

Figure 1:
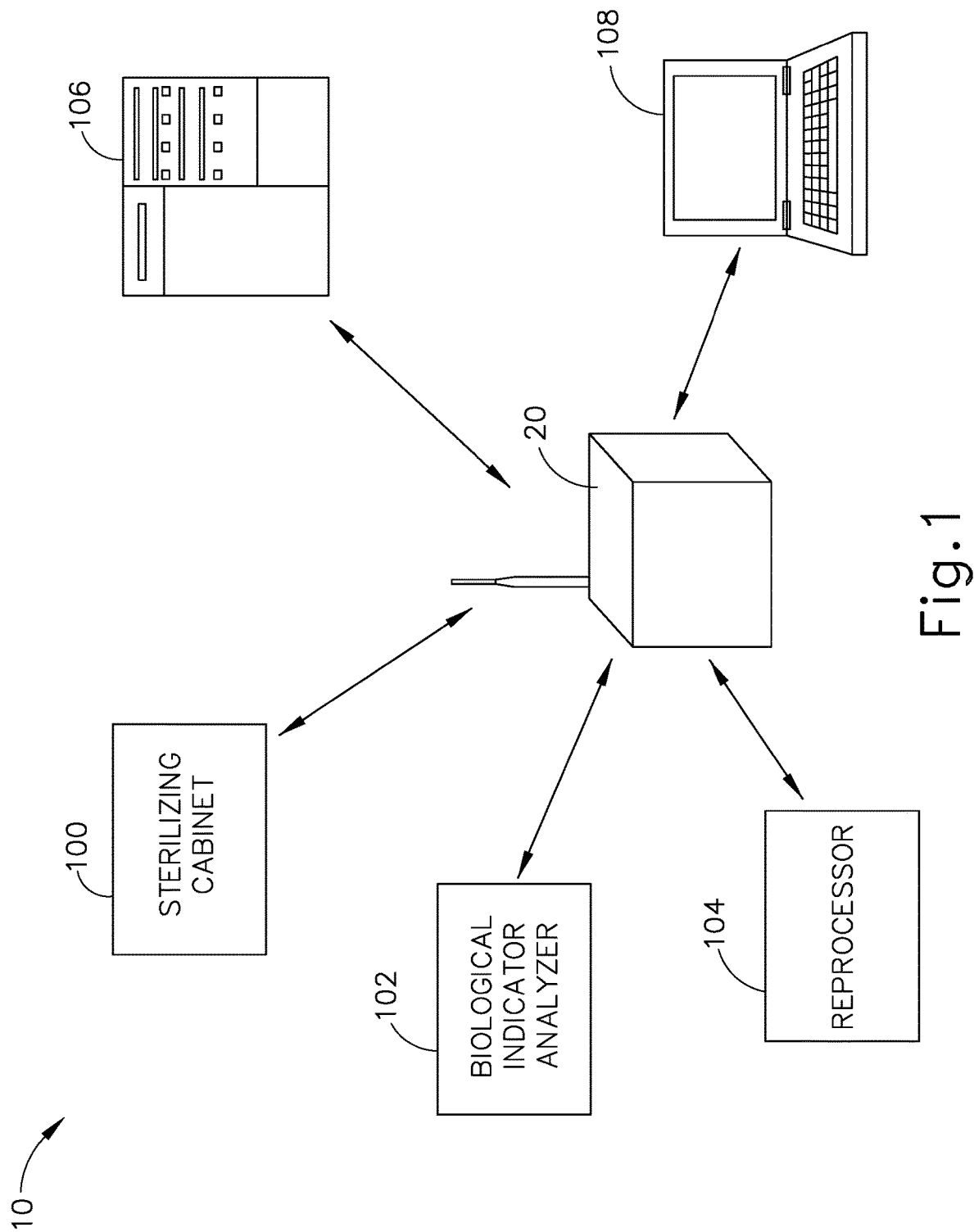
FIG. 1 depicts a schematic view of an exemplary sterilization system.

FIG. 1 depicts a schematic view of an exemplary system (10) of interconnected devices that may be configured to perform methods for sterilizing medical devices. System (10) of this example includes a sterilizing cabinet (100), a biological indicator analyzer (102), a medical device reprocessor (104), a communication hub (20), a server (106), and a user device (108). As will be described in greater detail below, sterilizing cabinet (100) may have a sealable sterilization chamber where contaminated medical devices may be placed. A user may interact with sterilizing cabinet (100) via a set of user inputs, such as physical buttons, a keyboard, a touch pad or mouse, other controls, and/or a touch screen display interface. A display of sterilizing cabinet (100) may provide users with information, configuration options, status and duration of sterilization cycles and preparation, and other similar information.

Sterilizing cabinet (100) is in communication with a server (106), such as a hospital record server or hospital local area network server. Server (106) may receive information from sterilizing cabinet (100) relating to sterilization procedures performed by the sterilizing cabinet (100), such as sterilization procedure durations and results; whether a particular sterilization procedure provided a subsequent indication of biological contamination; the identification of a user or technician who initiated, canceled, or complete a sterilization procedure; consumable materials or supplies used during a sterilization procedure; diagnostic information and systems errors; and/or other information. Server (106) may also provide information to the sterilizing cabinet (100) such as software updates, configuration updates, user authentication information, biological indicator use protocols, and other information. Communication between sterilizing cabinet (100) and server (106) may be accomplished via any suitable wired and/or wireless communication technology, such as Ethernet, Wi-Fi, Bluetooth, USB, infrared, NFC, and/or other technologies.

In system (10) of the present example, sterilizing cabinet (100) is also in communication with a communication hub (20), which itself is in communication with one or more biological indicator analyzers (102). As will be described in greater detail below, biological indicator analyzer (102) may comprise a desktop or wall mounted device that receives a biological indicator and measures one or more characteristics of the biological indicator in order to gather data that may be used to determine whether the biological indicator tests positive, indicating that contamination is present after a sterilization procedure; or negative, indicating that no contamination is present after the sterilization procedure.

In some versions, biological indicator analyzer (102) will measure and transmit data to communication hub (20), which will process the data to determine if there is contamination. In other versions, biological indicator analyzer (102) itself may both measure and analyze the data to determine whether there is contamination, and communication hub (20) may be used to receive, gather, and transmit such information to sterilizing cabinet (100) and/or other devices as will be described in greater detail below. In still other versions, biological indicator analyzer (102) and communication hub (20) may be different components of a single device; or may be components of sterilizing cabinet (100). Such variations may be desirable depending upon a particular implementation environment and user needs, such that a single device incorporating sterilizing cabinet (100), communication hub (20), and/or biological indicator analyzer (102) may be desirable in a semi-portable unit; while an implementation supporting a one-to-many relationship between sterilizing cabinet (100) and biological indicator analyzer (102) may be more advantageous for permanent installation in a large hospital with many users.

As will be described in greater detail below and as alluded to above, communication hub (20) is configured to process and relay information from biological indicator analyzer (102) to sterilizing cabinet (100). Biological indicator analyzer (102) and sterilizing cabinet (100) may each be coupled with communication hub (20) via any suitable wired and/or wireless communication technology, such as Ethernet, Wi-Fi, Bluetooth, USB, infrared, NFC, and/or other technologies. It should also be understood that communication hub (20) may be in communication with various other components, via wire or wirelessly, including but not limited to various user devices (108) such as desktop computers, laptop computers, mobile computing devices, smartphones, etc. Moreover, communication hub (20) may be in communication with server (106) via wire or wirelessly.

In versions where communication hub (20) is in communication with server (106), communication hub (20) may relay data, etc., between sterilizing cabinet (100) and server (106), such that communication hub (20) serves as an intermediary between sterilizing cabinet (100) and server (106). It should therefore be understood that, in some versions, sterilizing cabinet (100) may be in communication with server (106) via communication hub (20) instead of being directly in communication with server (106). Similarly, communication hub (20) may serve as an intermediary between sterilizing cabinet (100) and biological indicator analyzer (102); between sterilizing cabinet (100) and user device (108); between biological indicator analyzer (102) and server (106); between biological indicator analyzer (102) and user device (108); between reprocessor (104) and server (106); between reprocessor (104) and user device (108); and/or between user device (108) and server (106). Various suitable components and configurations that may be used to form communication hub (20) will be apparent to those of ordinary skill in the art in view of the teachings herein.

B. Exemplary Sterilizing Cabinet

Figure 2:
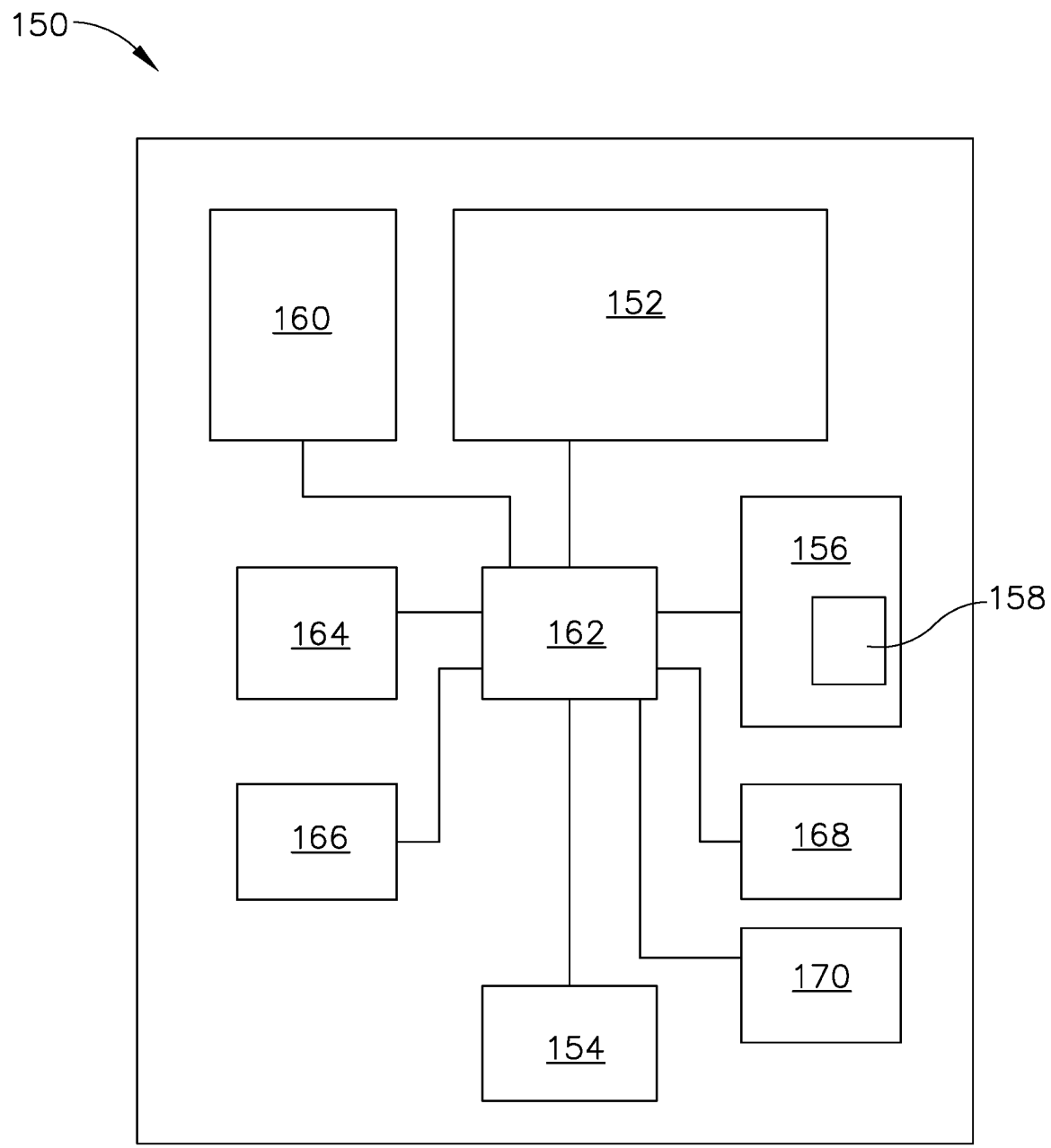
FIG. 2 depicts a schematic view of an exemplary sterilizing cabinet that may be used with the system of FIG. 1.

FIG. 2 depicts an exemplary set of components that may be incorporated into sterilizing cabinet (100) of system (10). In particular, FIG. 2 shows an exemplary sterilizing cabinet (150) that includes a sterilization chamber (152), which is configured to receive one or more medical devices for sterilization. While not shown, sterilizing cabinet (150) also includes a door that opens and closes sterilization chamber (152) in response to actuation of a kick plate (154). An operator may thereby open and close sterilization chamber (152) in a hands-free fashion. Sterilizing cabinet (100) also includes a sterilization module (156) that is operable to dispense a sterilant into sterilization chamber (152) in order to sterilize medical devices contained in sterilization chamber (152) as described above. In the present example, sterilization module (156) is configured to receive replaceable sterilant cartridges (158) containing a certain amount of sterilant. By way of example only, each sterilant cartridge (158) may contain enough sterilant to perform five sterilization procedures.

Sterilizing cabinet (150) of the present example further includes a touch screen display (160). Touch screen display (160) is operable to render various user interface display screens. Of course, touch screen display (160) may display various other screens as well. Touch screen display (160) is further configured to receive user input in the form of the user contacting touch screen display (160) in accordance with conventional touch screen technology. In addition, or in the alternative, sterilizing cabinet (150) may include various other kinds of user input features, including but not limited to buttons, keypads, keyboards, a mouse, a trackball, etc.

Sterilizing cabinet (150) of the present example further includes a processor (162), which is in communication with sterilization module (156) and with touch screen display (160). Processor (162) is operable to execute control algorithms to drive sterilization module (156) in accordance with user input. Processor (162) is further operable to execute instructions to display the various screens on touch screen display (160); and to process instructions received from a user via touch screen display (160) (and/or via other user input features). As will be described in greater detail below and as shown in FIG. 2, processor (162) is also in communication with various other components of sterilization cabinet (150) and is thereby operable to drive those components and/or process input and/or other data from those components. Various suitable components and configurations that may be used to form processor (162) will be apparent to those of ordinary skill in the art in view of the teachings herein.

Sterilizing cabinet (150) of the present example further includes a communication module (164). Communication module (164) is configured to enable bidirectional communication between sterilizing cabinet (150) and communication hub (20). In addition, or in the alternative, communication module (164) may be configured to enable bidirectional communication between sterilizing cabinet (150) and server (106). By way of example only, communication module (164) may be configured to provide wired and/or wireless communication via as Ethernet, Wi-Fi, Bluetooth, USB, infrared, NFC, and/or other technologies. Various suitable components and configurations that may be used to form communication module (164) will be apparent to those of ordinary skill in the art in view of the teachings herein. Communications that are sent from or received through communication module (164) are processed through processor (162).

Sterilizing cabinet (150) of the present example further includes an identification tag reader (166), which is operable to read an identification tag of a biological indicator as described herein. It should be understood that identification tag reader (166) may be used to perform the steps of indicator scanning. By way of example only, identification tag reader (166) may comprise an optical reader that is operable to read an optical identification tag (e.g., barcode, QR code, etc.) of a biological indicator. In addition, or in the alternative, identification tag reader (166) may comprise RFID reader that is operable to read an RFID identification tag (e.g., barcode, QR code, etc.) of a biological indicator. Various suitable components and configurations that may be used to form identification tag reader (166) will be apparent to those of ordinary skill in the art in view of the teachings herein. Data received through identification tag reader (166) is processed through processor (162). Examples of biological indicators that may be used with a sterilizing cabinet (150) may be found in U.S. patent application Ser. No. 15/057,768, entitled "Self-Contained Biological Indicator," filed Mar. 1, 2016, the disclosure of which is incorporated by reference herein. Other suitable forms that biological indicator may take will be apparent to those of ordinary skill in the art in view of the teachings herein.

Sterilizing cabinet (150) of the present example further includes a memory (168), which is operable to store control logic and instructions and that are executed by processor (162) to drive components such as sterilization module (156), touch screen display (160), communication module (164), and identification tag reader (166). Memory (168) may also be used to store results associated with setup of a sterilization cycle, performance of a load conditioning cycle, performance of a sterilization cycle, and/or various other kinds of information. Various suitable forms that memory (168) may take, as well as various ways in which memory (168) may be used, will be apparent to those of ordinary skill in the art in view of the teachings herein.

Sterilizing cabinet (150) of the present example further includes a printer (170), which is operable to print information such as results associated with setup of a sterilization cycle, performance of a load conditioning cycle, performance of a sterilization cycle, and/or various other kinds of information. By way of example only, printer (170) may comprise a thermal printer, though of course any other suitable kind of printer may be used. Various suitable forms that printer (170) may take, as well as various ways in which printer (170) may be used, will be apparent to those of ordinary skill in the art in view of the teachings herein. It should also be understood that printer (170) is merely optional and may be omitted in some versions.

Figure 3:
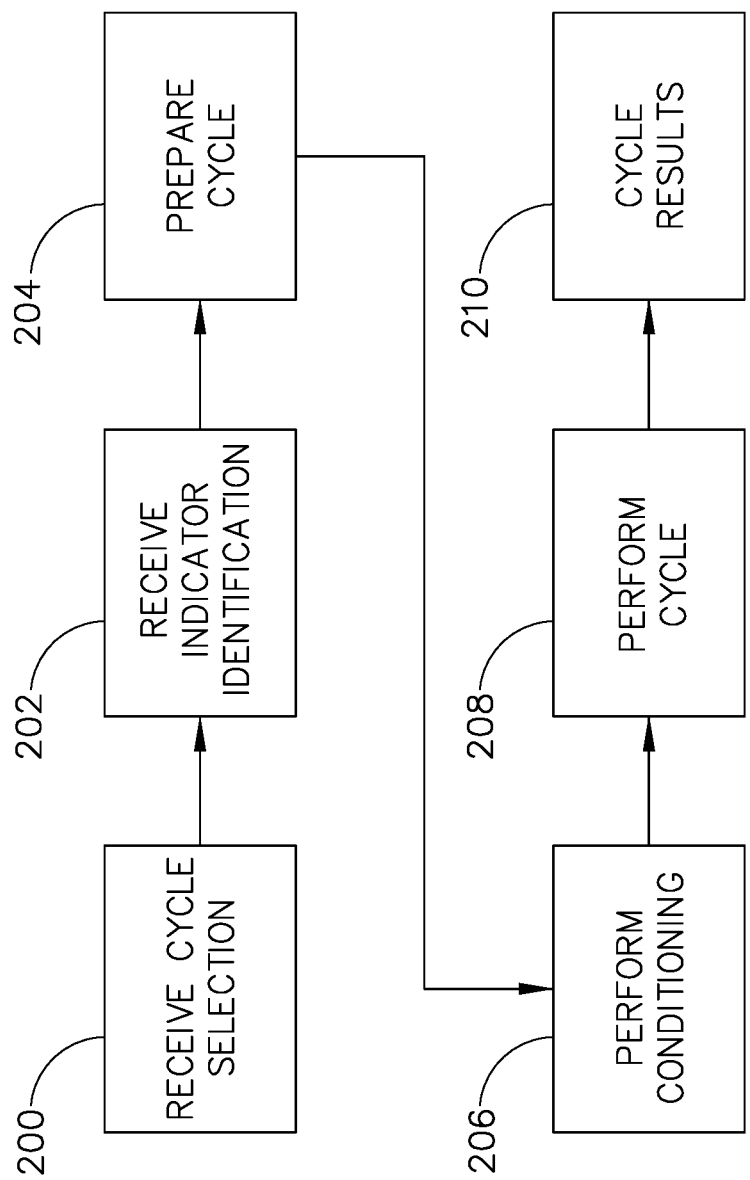
FIG. 3 depicts a high level flowchart of an exemplary set of steps that the sterilizing cabinet of FIG. 2 could perform to sterilize a medical device.

FIG. 3 depicts a high level flowchart of an exemplary set of steps that system (10) could perform to sterilize a medical device. A user may interact with the system via a user interface such as a keyboard or touch screen of sterilizing cabinet (100), as will be described in greater detail below; or via an input device in communication with sterilizing cabinet (100). Initially, sterilizing cabinet (100) may display one or more sterilization cycles via a display and then receive a sterilization cycle selection (block 200) from the user. Sterilizing cabinet (100) may be configured to perform one or more sterilization cycles, with different sterilization cycles being appropriate for different types and quantities of medical devices.

Sterilizing cabinet (100) may also display instructions indicating whether a biological indicator should be used with the selected sterilization cycle, and receive a biological indicator identification (block 202). A biological indicator may be placed inside a sterilization chamber of sterilizing cabinet (100) before the sterilization cycle begins and may remain in the sterilization chamber during a sterilization cycle. The user may thus identify the particular biological indicator (block 202) before the biological indicator is placed in the sterilization chamber. The biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but may be required based on hospital rules or local regulations. When used, a biological indicator may be identified by manual input, such as keyboard entry of a biological indicator type or identifier; or may be identified automatically, such as by an optical scan of an optical identifier or a wireless scan of an RFID or other unique identifier.

Selection of a sterilization cycle (block 200) and identification of a biological indicator (block 202) may define one or more requirements for the configuration and arrangement of medical devices within sterilizing cabinet (100). A door of the sterilization chamber of sterilizing cabinet (100) may be opened and instructions may be displayed to guide a user through preparation of the sterilization cycle (block 204), including placement of the biological indicator, placement of medical devices, closing the door of the sterilization chamber of the sterilization cabinet (100), and/or other changes in preparation. Before initiating the actual sterilization cycle (block 208), sterilization cabinet (100) may also perform load conditioning (block 206) of the medical devices that are loaded in the sterilization chamber of the sterilization cabinet (100). Such load conditioning (block 206) may include verifying that the sterilization chamber is sealed; verifying contents of the sterilization chamber; checking physical characteristics of the contents of the sterilization chamber such as moisture levels, content volume, content weight, internal temperature, or other characteristics; and/or performing one or more conditioning steps that may include heat treatment, chemical treatment, plasma treatment, or other types of treatment to reduce moisture, raise temperature, and/or otherwise prepare the medical devices in the sterilization chamber for the sterilization cycle.

Once the load conditioning (block 206) has been completed, the selected sterilization cycle itself may be performed (block 208). The sterilization cycle (block 208) may include exposing the medical device(s) in the sterilizing chamber to pressurized sterilant gas, further heat treatment, chemical treatment, plasma treatment, vacuum treatment, and/or other types of sterilization procedures. After the sterilization cycle (block 208) is completed, the complete sterilization results may be displayed to a user via a display of the sterilization cabinet; transmitted to server (106); printed locally; and/or displayed, transmitted, and/or stored via other devices as may be desirable.

Sterilization cabinet (100) may also provide results (block 210) of the sterilization cycle. This provision of results (block 210) may include results from analysis of a biological indicator via biological indicator analyzer (102) as described below. These results may include a positive or negative indication of contamination present in the biological indicator at the completion of the sterilization cycle (block 208). In cases where the biological indicator suggests that contamination is present after completion of the sterilization cycle (block 208), additional actions may be taken such as alerting a user of the positive test and analysis of sterilization cycle history in order to determine if other past cycles may be the cause of the contamination; and/or if subsequently sterilized medical devices may need to be re-sterilized.

In addition to the foregoing, sterilizing cabinet (150) may be configured and operable in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein. An example of a commercially available sterilizing cabinet (150) is the STERRAD® System by Advanced Sterilization Products of Irvine, Calif. Other suitable ways in which sterilizing cabinet (150) may be configured and operable will be apparent to those of ordinary skill in the art in view of the teachings herein.

C. Exemplary Biological Indicator Analyzer

Figure 4:
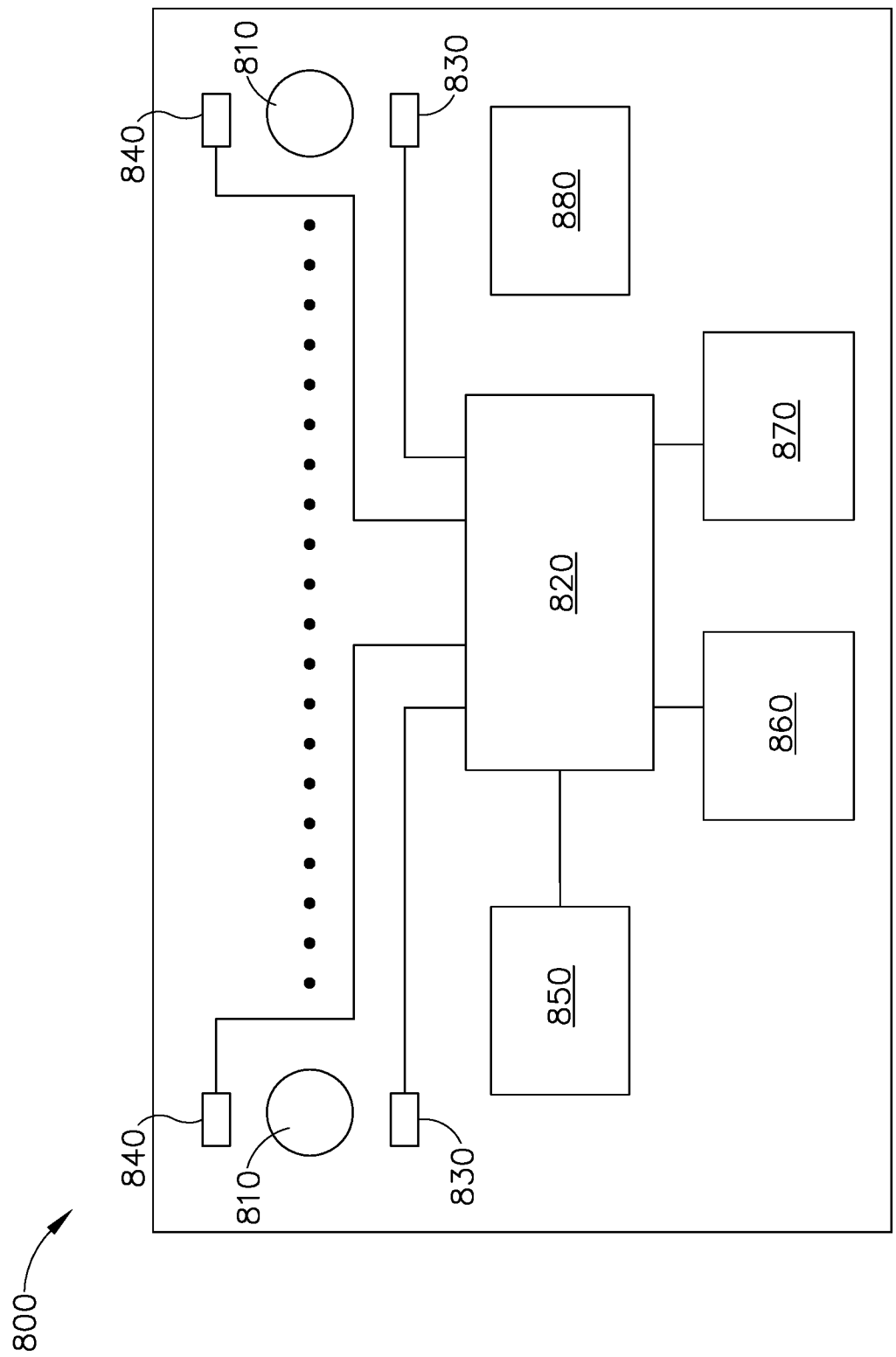
FIG. 4 depicts a schematic view of an exemplary indicator analyzer that may be used to process a biological indicator assembly as part of the system of FIG. 1.

FIG. 4 depicts an exemplary set of components that may be incorporated into biological indicator analyzer (102). In particular, FIG. 4 shows an exemplary biological indicator analyzer (800) that is operable to perform a biological indicator analysis. Biological indicator analyzer (800) of this example comprises a plurality of wells (810), each of which is configured to insertingly receive a respective biological indicator. While two wells (810) are shown, it should be understood that any other suitable number of wells (810) may be provided, including eight wells (810), less than eight wells (810), or more than eight wells (810). Biological indicator analyzer (800) also includes a processor (820) that is operable to execute instructions and control algorithms, process information, etc.

Each well (810) has an associated light source (830) and sensor (840). Each light source (830) is configured to project light through a housing of the biological indicator that is inserted in the corresponding well (810); and each sensor (840) is operable to detect light fluoresced by fluid contained in the housing. By way of example only, light source (830) may be in the form of a laser that is configured to emit ultraviolet light. Various other suitable forms that light source (830) may take will be apparent to those of ordinary skill in the art in view of the teachings herein. By way of further example only, sensor (840) may comprise a charge coupled device (CCD). Various other suitable forms that sensor (840) may take will be apparent to those of ordinary skill in the art in view of the teachings herein. As noted above, the fluorescence of the fluid will depend on the amount of living microorganisms contained in the medium of the fluid. Thus, sensor (840) will be able to detect the presence of living microorganisms in the fluid based on the degree to which the fluid fluoresces in response to light from light source (830).

Biological indicator analyzer (800) of the present example further includes a touch screen display (850). Touch screen display (850) is operable to render various user interface display screens associated with operation of biological indicator analyzer (800). Touch screen display (850) is further configured to receive user input in the form of the user contacting touch screen display (850) in accordance with conventional touch screen technology. In addition, or in the alternative, biological indicator analyzer (800) may include various other kinds of user input features, including but not limited to buttons, keypads, keyboards, a mouse, a trackball, etc. Displays provided through touch screen display (850) may be driven by processor (820). User inputs received through touch screen display (850) may be processed by processor (820).

Biological indicator analyzer (800) of the present example further includes a communication module (860). Communication module (860) is configured to enable bidirectional communication between biological indicator analyzer (800) and communication hub (20). In addition, or in the alternative, communication module may be configured to enable bidirectional communication between biological indicator analyzer (800) and server (106). By way of example only, communication module (860) may be configured to provide wired and/or wireless communication via as Ethernet, Wi-Fi, Bluetooth, USB, infrared, NFC, and/or other technologies. Various suitable components and configurations that may be used to form communication module (860) will be apparent to those of ordinary skill in the art in view of the teachings herein. Communications that are sent from or received through communication module (860) are processed through processor (820).

Biological indicator analyzer (800) of the present example further includes an identification tag reader (870), which is operable to read an identification tag of the biological indicator as described herein. It should be understood that identification tag reader (870) may be used to identify the biological indicator before the biological indicator is analyzed. By way of example only, identification tag reader (870) may comprise an optical reader that is operable to read an optical identification tag (e.g., barcode, QR code, etc.) of a biological indicator. In addition, or in the alternative, identification tag reader (870) may comprise RFID reader that is operable to read an RFID identification tag (e.g., barcode, QR code, etc.) of a biological indicator. Various suitable components and configurations that may be used to form identification tag reader (870) will be apparent to those of ordinary skill in the art in view of the teachings herein. Data received through identification tag reader (870) is processed through processor (820).

Biological indicator analyzer (800) of the present example further includes a memory (880), which is operable to store control logic and instructions and that are executed by processor (820) to drive components such as light source (830), touch screen display (850), communication module (860), and identification tag reader (870). Memory (880) may also be used to store results associated with performance of biological indicator analysis, and/or various other kinds of information. Various suitable forms that memory (880) may take, as well as various ways in which memory (880) may be used, will be apparent to those of ordinary skill in the art in view of the teachings herein.

Figure 5:
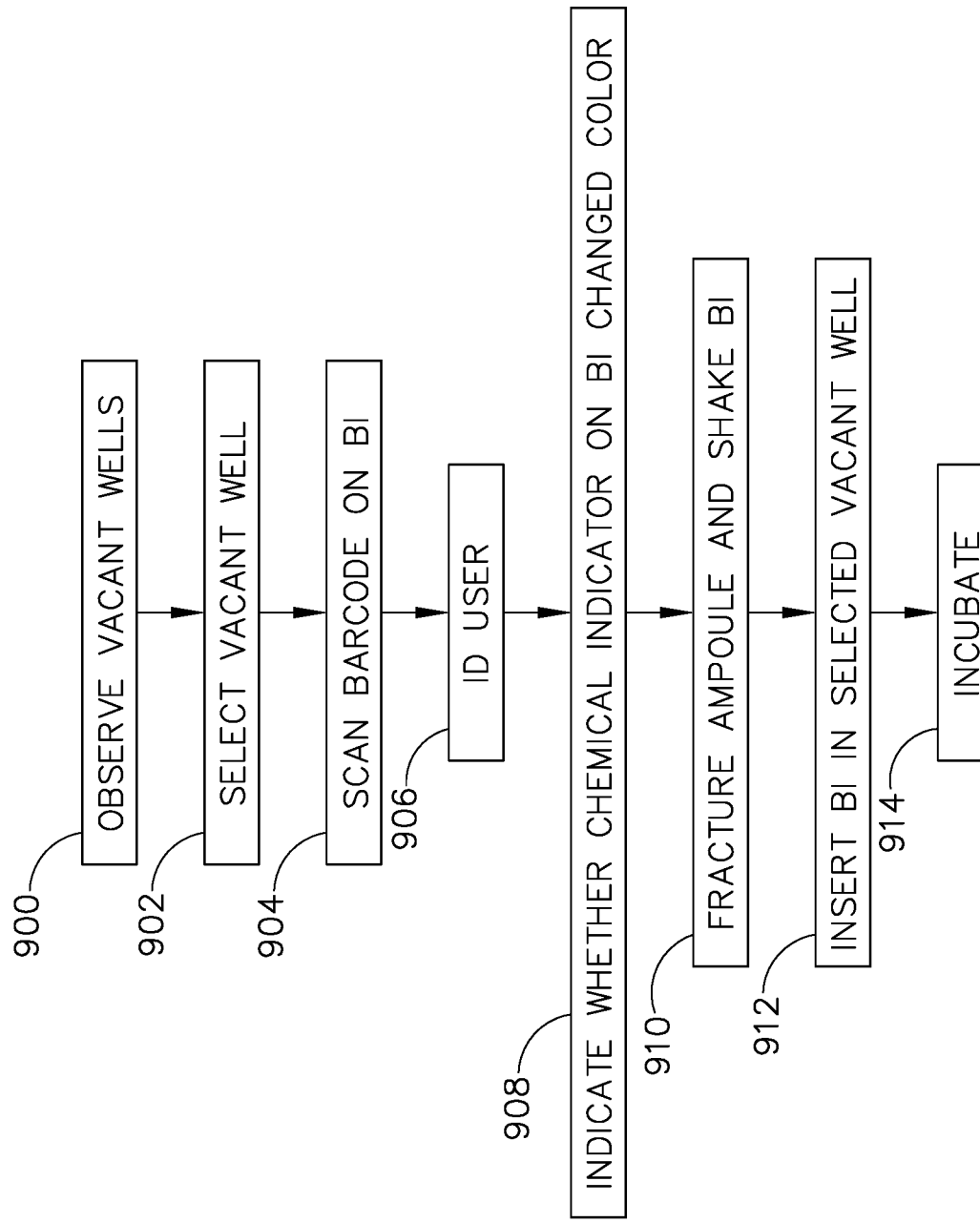
FIG. 5 depicts a flowchart of exemplary steps that may be performed by the indicator analyzer of FIG. 4 in preparation for analysis of a biological indicator.

FIG. 5 shows an exemplary set of steps that may be used to initiate biological indicator analysis cycle by biological indicator analyzer (102, 800). As a first step, the user may observe which wells (810) are vacant (block 900) and select a vacant well (block 902). In some versions, touch screen display (850) presents a number next to each vacant well (810), such that the operator simply touches the number associated with the selected vacant well (810) in order to effect selection of that vacant well (block 902). Next, a display screen on touch screen display (850) may prompt the user to place the identification tag of biological indicator near reader (870) to enable reader (870) to read the identification tag of biological indicator. As part of this prompting, touch screen display (850) may point to the location of reader (870) to assist the user in finding reader (870). The user may then use reader (870) to read the identification tag of biological indicator (block 904).

A display screen on touch screen display (850) may then prompt the user to identify himself or herself. The user may then manipulate touch screen display (850) to identify himself or herself (block 906). A display screen on touch screen display (850) may then prompt the user to indicate whether the chemical indicator on cap of biological indicator has changed color. The user may then manipulate touch screen display (850) to indicate whether the chemical indicator on cap of biological indicator has changed color (block 908).

A display screen on touch screen display (850) may then prompt the user to prepare biological indicator for loading into the selected well (810) by fracturing ampoule and shaking biological indicator. The operator may then fracture ampoule by pressing on cap, then shake biological indicator (block 910) to ensure proper mixing of fluid with carrier. The user may then quickly place biological indicator in the selected well (810) (block 912). In some instances it may be desirable to insert biological indicator in the selected well (810) (block 912) immediately after fracturing ampoule and shaking biological indicator (block 910).

In some versions, indicator analyzer (102, 800) is configured to determine whether the user appropriately completed the step of fracturing ampoule and shaking biological indicator (block 910) before inserting biological indicator in the selected well (810) (block 912). By way of example only, this may be determined based on how sensor (840) detects light emitted by light source (830) after biological indicator is inserted in the selected well (810). In the event that indicator analyzer (102, 800) determines that the user failed to appropriately complete the step of fracturing ampoule and shaking biological indicator (block 910) before inserting biological indicator in the selected well (810) (block 912), touch screen display (850) may prompt the user to withdraw biological indicator from well (810) and properly complete the step of fracturing ampoule and shaking biological indicator (block 910).

To the extent that the user has properly completed the step of fracturing ampoule and shaking biological indicator (block 910), and then inserted biological indicator in the selected well (block 912), biological indicator is allowed to sit in well (810) for an incubation period (block 914). During the incubation period (block 914), light source (830) associated with the selected well (810) is activated and sensor (840) monitors responsive fluorescence of fluid in indicator. Well (810) may also be heated (e.g., to approximately 60° C.) during the incubation period (block 914). As noted above, fluid includes a fluorophore whose fluorescence depends on the amount of microorganisms contained in the medium. Thus, sensor (840) can detect the presence of living microorganisms (from carrier) in fluid based on the fluorescence of fluid. It should therefore be understood that, after a suitable incubation period has passed, indicator analyzer (102, 800) will conclude whether any of the microorganisms that were on carrier (i.e., before the sterilization cycle in sterilization cabinet (100, 150)) survived the sterilization cycle in sterilization cabinet (100), based on the fluorescence of fluid as sensed by sensor (840).

By way of example only, the incubation period (block 914) may be approximately 30 minutes. Alternatively, the incubation period may be substantially longer (e.g., one or more hours), shorter, or of any other suitable duration. During the incubation period (block 914), touch screen display (850) may provide a graphical representation of the amount of time remaining in the incubation period. When more than one well (810) is occupied by a corresponding biological indicator, touch screen display (850) may provide a graphical representation of the amount of time remaining in the incubation period for each occupied well (810).

Figure 6:
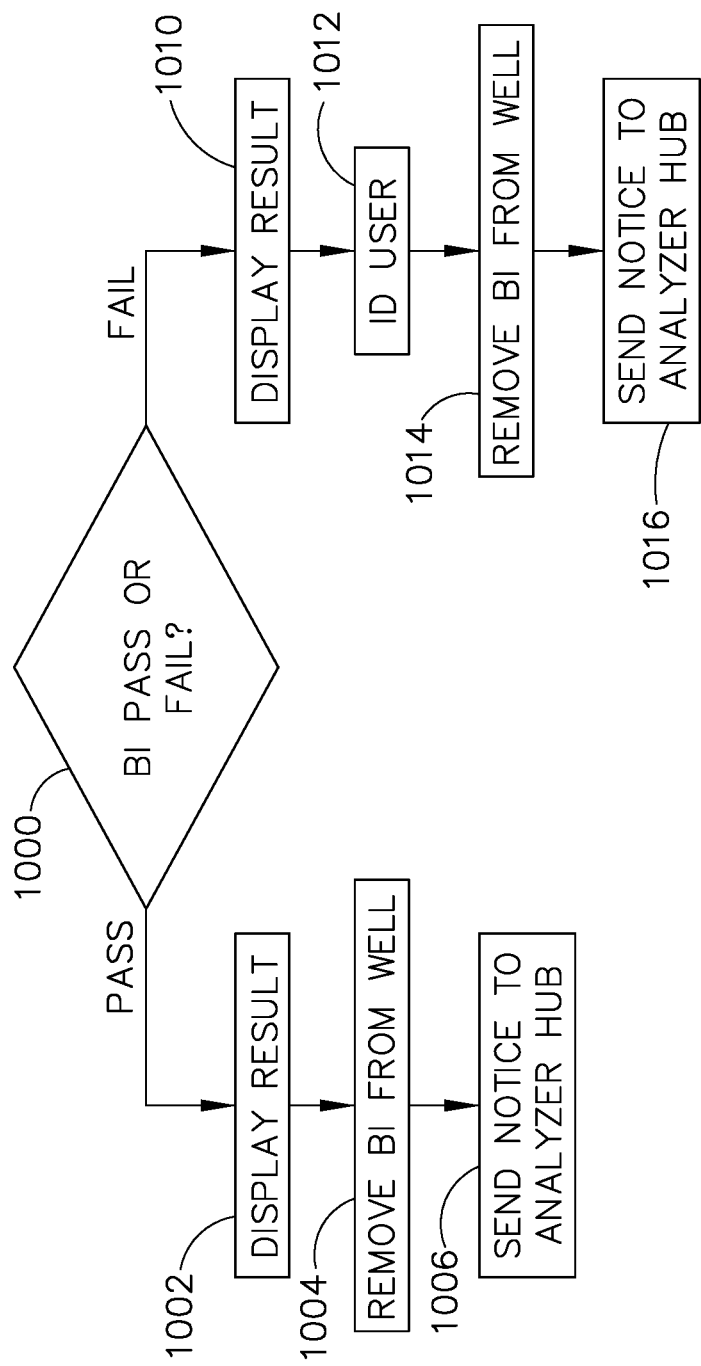
FIG. 6 depicts a flowchart of exemplary steps that may be performed by the indicator analyzer of FIG. 4 based on whether a biological indicator passes or fails analysis.

FIG. 6 shows a set of exemplary steps that may be carried out once the incubation period (block 914) is complete. As noted above, biological indicator analyzer (102, 800) can determine whether any of the microorganisms that were on carrier (i.e., before the sterilization cycle in sterilization cabinet (100, 150)) survived the sterilization cycle in sterilization cabinet (100), based on the fluorescence of fluid as sensed by sensor (840). Thus, biological indicator analyzer (102, 800) can determine whether biological indicator passes or fails analysis (block 1000). In this sense, a "pass" result indicates that no living microorganisms are present in biological indicator, which indicates that the sterilization cycle (block 208) in sterilization cabinet (100) was successful. A "fail" result indicates that living microorganisms are present in biological indicator, which indicates that the sterilization cycle (block 208) in sterilization cabinet (100) was unsuccessful.

In the event of a "pass" result, touch screen display (850) may present a screen to the user indicating that biological indicator passed the analysis (block 1002). Touch screen display (850) may also prompt the user to remove biological indicator from well (810) (block 1004) and appropriately discard the used biological indicator. As described in greater detail below, biological indicator analyzer (102, 800) may also transmit the "pass" result (and associated data) to communication hub (20) (block 1006) via communication module (860). In some versions, this transmission of the "pass" result (and associated data) to communication hub (20) (block 1006) is done in response to a query from communication hub (20), such that the "pass" result (and associated data) is pulled from biological indicator analyzer (102, 800) by communication hub (20). In some other versions, the "pass" result (and associated data) is pushed to communication hub (20) (block 1006) by biological indicator analyzer (102, 800), without requiring a query from communication hub (20).

In the event of a "fail" result, touch screen display (850) may present a screen to the user indicating that biological indicator failed the analysis (block 1010). Touch screen display (850) may then prompt the user to identify himself or herself. The user may then manipulate touch screen display (850) to identify himself or herself (block 1012). Touch screen display (850) may then prompt the user to remove biological indicator from well (810) (block 1014) and appropriately discard the used biological indicator. As described in greater detail below, biological indicator analyzer (102, 800) may also transmit the "fail" result (and associated data) to communication hub (20) (block 1016) via communication module (860). In some versions, this transmission of the "fail" result (and associated data) to communication hub (20) (block 1016) is done in response to a query from communication hub (20), such that the "fail" result (and associated data) is pulled from biological indicator analyzer (102, 800) by communication hub (20). In some other versions, the "fail" result (and associated data) is pushed to communication hub (20) (block 1016) by biological indicator analyzer (102, 800), without requiring a query from communication hub (20).

D. Exemplary Medical Device Reprocessor

Reprocessor (104) of the present example is configured to reprocess (i.e., decontaminate) medical devices such as endoscopes. In particular, reprocessor (104) is configured to enclose a used or otherwise non-sterile endoscope in a sealed chamber; flush the internal lumen(s) of the endoscope with detergent, water, alcohol, and/or various other liquids; spray the exterior of the endoscope with detergent, water, alcohol, and/or various other liquids; and dry the interior and exterior of the endoscope. In some instances, while the endoscope has not necessarily been sterilized, the endoscope may nevertheless be ready for use in another medical procedure after having been reprocessed through reprocessor (104).

By way of example only, reprocessor (104) may be configured and operable in accordance with at least some of the teachings of U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; U.S. Pat. No. 8,246,909, entitled "Automated Endoscope Reprocessor Germicide Concentration Monitoring System and Method," issued Aug. 21, 2012, the disclosure of which is incorporated by reference herein; and/or U.S. patent application Ser. No. 15/157,800, entitled "Apparatus and Method for Reprocessing a Medical Device," filed May 20, 2016, the disclosure of which is incorporated by reference herein. An example of a commercially available reprocessor (104) is the EVOTECH® Endoscope Cleaner and Reprocessor (ECR) by Advanced Sterilization Products of Irvine, Calif. Other suitable ways in which reprocessor (104) may be configured and operable will be apparent to those of ordinary skill in the art in view of the teachings herein.

It should also be understood that some medical devices (e.g., endoscopes) may be processed in reprocessor (104) without also being processed in sterilizing cabinet (100, 150). Likewise, some medical devices (e.g., endoscopes) may be processed in sterilizing cabinet (100, 150) without also being processed in reprocessor (104). The decision on whether to process a medical device such as an endoscope through sterilizing cabinet (100, 150) or reprocessor (104) may be based on the kind of endoscope at hand and/or based on the location(s) within the patient anatomy in which the endoscope is typically used.

E. Exemplary Communication Hub

Figure 7:
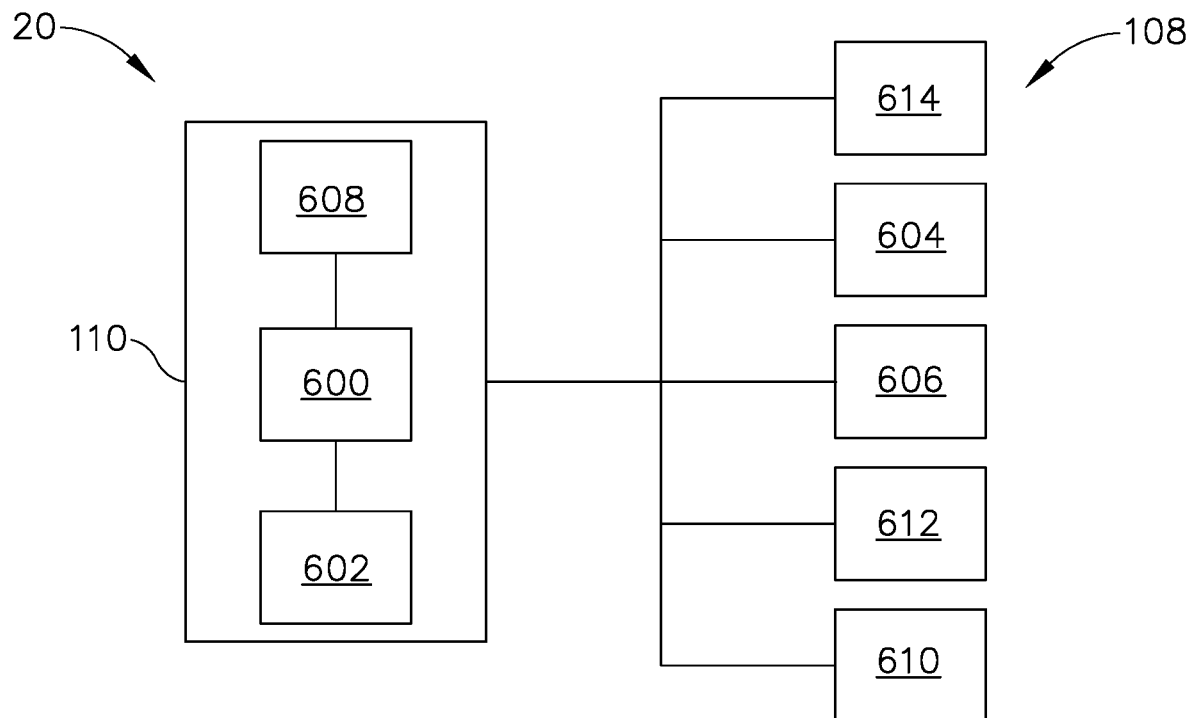
FIG. 7 depicts a schematic view of an exemplary communication hub that may be used to provide monitoring of and communications with one or more other devices within the system of FIG. 1 via a user device.

FIG. 7 shows a schematic view of an exemplary communication hub (20) that may be used within system (10) to provide monitoring of and communication with one or more other devices (100, 102, 106) via a user device (108). Communication hub (20) shown in FIG. 7 includes a housing or case (110) containing a processor (600) and memory (602) for storing and manipulating data, and a network interface (608) for communicating with outside devices such as the various devices (100, 102, 106, 108) shown in FIG. 1. Memory (602) may include one or more of a random access memory, a read only memory, a volatile memory, a non-volatile memory, an internal hard drive, an external hard drive, a USB storage device, a flash memory storage device, a network storage device, and/or other similar forms of memory. Network interface (608) may allow a wired connection between two or more devices, such as by Ethernet, USB, fiber optic, and/or other wired data transmission medium; and/or may allow wireless connection between two or more devices, such as by Wi-Fi, Bluetooth, radio transmission, or other wireless data transmission medium.

FIG. 7 shows a version of a communication hub (20) that does not have a display, keyboard, or other interface that a user directly interacts with. Instead, that communication hub (20) may be in communication with a user device (108) via the network interface (608), and a user may interact with the communication hub (20) via a display (606) and user input (604) of the user device (108). In this manner, the communication hub (20) may provide information to the user device (108), which the user device (108) may render via a display (606) such as a computer monitor or mobile device touch screen. Communication hub (20) may further receive user input from the user device (108) via a user input (604) such as a keyboard, mouse, or other input device. This allows a user to, for example, use a device (108) such as a laptop computer to view information and configurations of other devices in communication with hub (20), such as sterilizing cabinet (100) and biological indicator analyzer (102), on the laptop display (606); and to navigate and modify such configurations and information via the laptop keyboard and mouse (604).

Other devices or features that may be present in a user device (108) or connected to a user device include an alternate input (614) such as an imaging scanner, microphone, NFC or RFID scanner, and similar input devices, a printer (612), and an alternate output device (610), such as a speaker, indicator light, vibration function, or similar output devices. With such additional devices or features, information and configuration from devices connected to communication hub (20) may be printed via a printer (612) so that hard copies are available. An alternate user input (614) such as an imaging scanner may be used to read barcodes or other image identifiers from a device to assist in identifying devices, connecting to devices, or changing configurations on devices. An alternate output (610) may be used to provide additional forms of notification or feedback to a user, such as providing an audible alarm when a device unexpectedly loses connection to communication hub (20).

Other examples of devices or features that may be present in communication hub (20) or a user device (108) in communication with hub (20) will be apparent to those of ordinary skill in the art in light of the disclosure herein.

Figure 8:
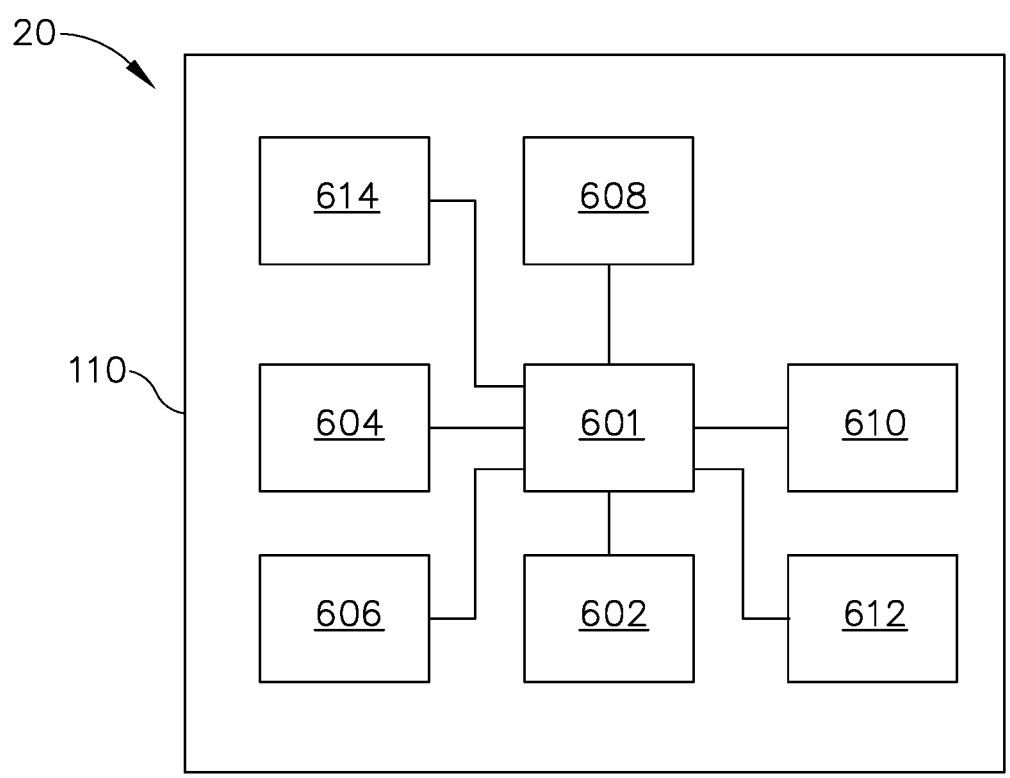
FIG. 8 depicts a schematic view of an exemplary alternative communication hub that may be used to provide monitoring of and communications with one or more other devices.

While such features and components may be spread across several devices, such as a combination of a communication hub (20) and user device (108) as shown in FIG. 7, such features and components may alternatively be integrated into a single device such as the communication hub (20) of FIG. 8. In the exemplary hub of FIG. 8, communication hub (20) may be a proprietary device such as a kiosk or other piece of specialized equipment, or may be a computer or server configured with additional components. Such a communication hub (20) may contain or be directly connected to a processor (601), memory (602), user interface (604), display (606), network interface (608) alternate output (610), printer (612), and alternate input (614) having the capabilities described above or otherwise as will be apparent to one of ordinary skill in the art in light of the disclosure herein. Such a communication hub (20) could be, for example, a specially built kiosk containing one or more of the listed components in a single case, body, or frame, but could also include, for example, a computer or server having a memory, processor, and wireless communication expansion card configured to serve as a communication router for devices it is in wireless communication with. Other variations exist, and a particular implementation of a communication hub (20) and available features will depend upon such factors as desired cost, setting, use, and other factors.

Figure 9:
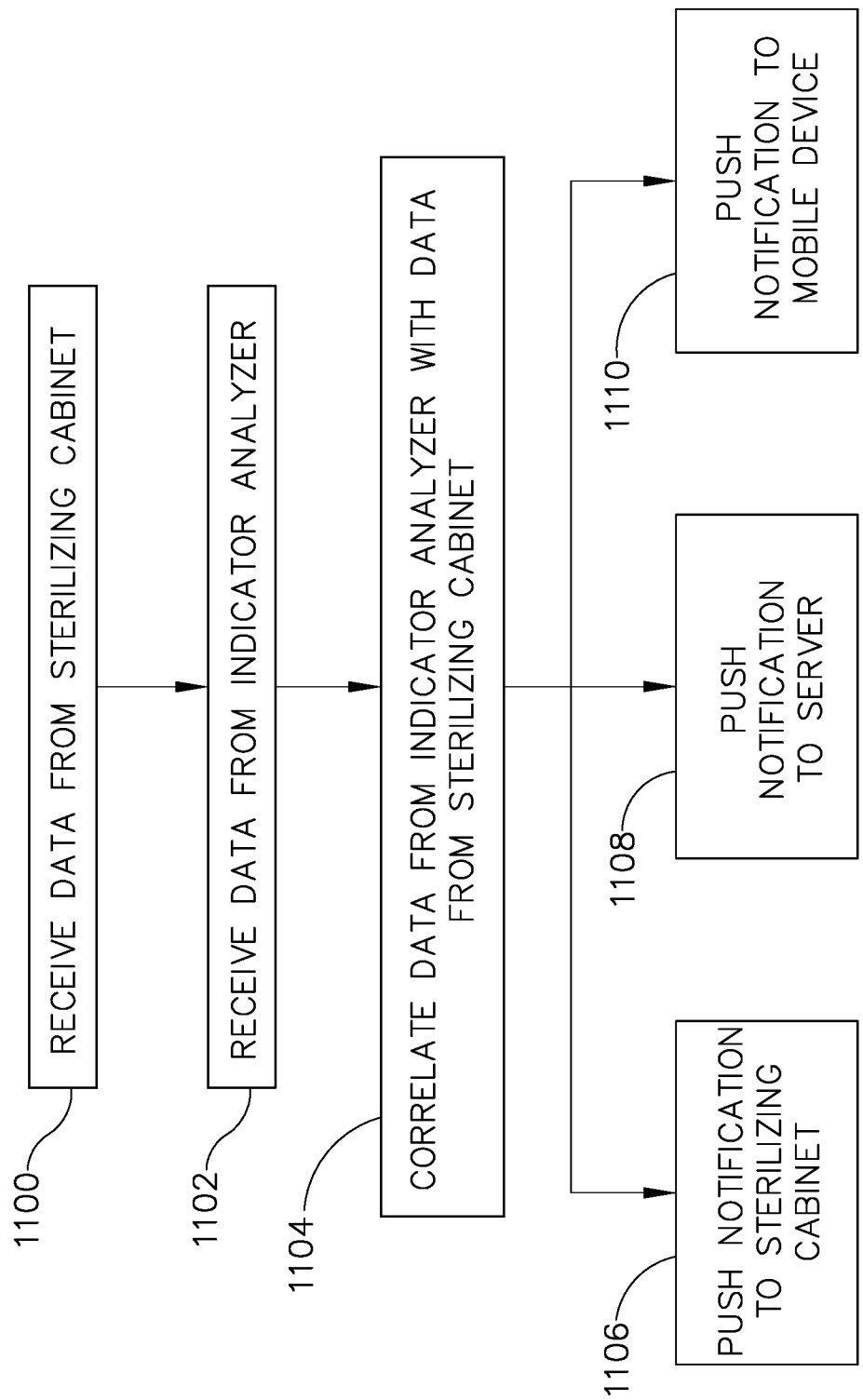
FIG. 9 depicts a flowchart of exemplary steps that may be performed by a communication hub of the system of FIG. 1.

FIG. 9 shows a set of exemplary steps that may be performed by communication hub (20). As noted above, communication hub (20) may be in communication with sterilizing cabinet (100, 150) via communication module (164). Communication hub (20) may thus receive data from sterilizing cabinet (100, 150) (block 1100). By way of example only, and as noted above, this data may include information relating to a sterilization cycle (block 210). As also noted above, communication hub (20) may be in communication with biological indicator analyzer (102, 800) via communication module (860). Communication hub (20) may thus receive data from biological indicator analyzer (102, 800). By way of example only, and as noted above, this data may include information relating to passage of a biological indicator analysis (block 1006) or failure of a biological indicator analysis (block 1016). While communication hub (20) is shown as only being in communication with one sterilizing cabinet (100, 150) and with one biological indicator analyzer (102, 800), it should be understood that a single communication hub (20) may be in communication with several sterilizing cabinets (100, 150) and/or several biological indicator analyzers (102, 800).

Communication hub (20) may further process the data received from sterilizing cabinet (100, 150) and biological indicator analyzer (102, 800) by correlating the data (block 1104). By way of example only, when communication hub (20) receives a notification from biological indicator analyzer (102, 800) that a particular biological indicator failed a biological indicator analysis (block 1016), regardless of whether this information is pushed to communication hub (20) or pulled by communication hub (20), communication hub (20) may correlate the identity of that particular biological indicator with a particular sterilizing cabinet (100, 150). Communication hub (20) may further correlate the identity of that particular biological indicator with particular sterilization cycles performed by that particular sterilizing cabinet (100, 150). With this correlated information, communication hub (20) may identify sterilization cycles whose success may be questionable, such that the sterility of the medical devices that were purportedly sterilized during such sterilization cycles is also questionable.

Having identified sterilization cycles whose success may be questionable, and thus medical devices whose sterility may be questionable, communication hub (20) may automatically send out notifications to various other devices in order to prevent such medical devices from being used before being put through another sterilization process. By way of example only, communication hub (20) may push a notification to sterilizing cabinet (100, 150) (block 1106) indicating the sterilization cycles whose success may be questionable, and thus medical devices whose sterility may be questionable. Sterilizing cabinet (100, 150) may relay this notification to a user by presenting an interface via touch screen display (160).

In addition or in the alternative, communication hub (20) may push a notification to server (106) (block 1108) indicating the sterilization cycles whose success may be questionable, and thus medical devices whose sterility may be questionable. Of course, communication hub (20) may also push a notification to server (106) indicating when a biological indicator passed analysis (block 1000) and/or other information associated with operation of sterilizing cabinet (100, 150) and/or biological indicator analyzer (102, 800).

In addition or in the alternative, communication hub (20) may push a notification to one or more mobile devices (block 1110), such as an operator of system (10), etc., indicating the sterilization cycles whose success may be questionable, and thus medical devices whose sterility may be questionable. In some versions, communication hub (20) pushes such notifications to a mobile device associated with a person who was identified as a user of sterilizing cabinet (100, 150) and/or a person who was identified as a user of biological indicator analyzer (102, 800) (e.g., during the user identification step (block 906)). Of course, communication hub (20) may also push a notification to one or more mobile devices indicating when a biological indicator passed analysis (block 1000) and/or other information associated with operation of sterilizing cabinet (100, 150) and/or biological indicator analyzer (102, 800).

Other suitable ways in which communication hub (20) may push notifications to other devices will be apparent to those of ordinary skill in the art in view of the teachings herein.

It should also be understood that communication hub (20) may be used to provide software updates, firmware updates, and other information to sterilizing cabinet (100, 150) and/or biological indicator analyzer (102, 800). As another merely illustrative example, communication hub (20) may be used to provide hospital policy information to sterilizing cabinet (100, 150), such as hospital policy relating to the frequency of use of biological indicators. Other suitable ways in which communication hub (20) may be used will be apparent to those of ordinary skill in the art in view of the teachings herein.

F. Exemplary User Device

User device (108) may comprise a device such as a laptop computer, a desktop computer, a mobile device such as a smartphone, tablet, or other mobile computing device, or a proprietary device having similar capabilities, such capabilities including wired or wireless communication with devices such as communication hub (20), a processor and memory, a display, a user interface, and other capabilities as may be described in further detail below. User device (108) may be used to access and view information associated with one or more processing components (100, 102, 104, 150,

800) via communication hub (20), and may also be used to create or modify configurations and settings of communication hub (20) and connected devices. A user of user device (108) may view information and configure devices via, for example, a desktop software application, a mobile device software application, a web browser, or another software interface that may allow user device (108) to exchange information with communication hub (20). While only one user device (108) is shown in FIG. 1 and in FIG. 4 as being in communication with communication hub (20), it should be understood that several user devices (108) may be in communication with communication hub (20). Similarly, several sterilizing cabinets (100), several biological indicator analyzers (102), and/or several servers (106) may be in communication with communication hub (20).

II. Exemplary Methods and Interfaces of Communication Hub

Figure 10:
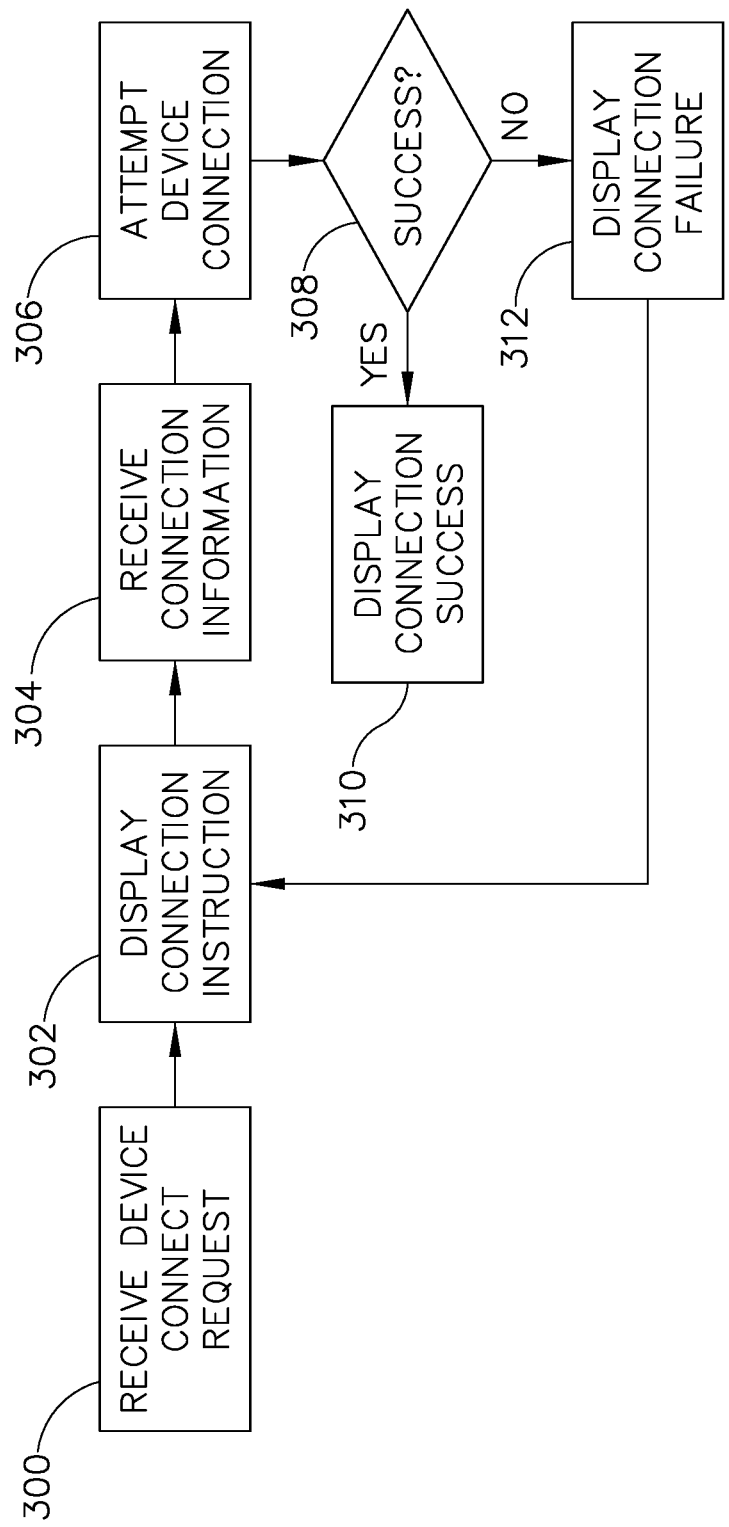
FIG. 10 shows an exemplary set of steps that may be performed using a communication hub, such as that shown in FIG. 7 or that shown in FIG. 8, to manage connections between the communication hub and one or more medical device processing components.

FIG. 10 shows an exemplary set of steps that may be performed using a communication hub (20) such as that shown in FIG. 7-8 to manage connections between the communication hub (20) and one or more processing components (100, 102, 104, 150, 800). These steps may be performed at various times, such as when a new processing component (100, 102, 104, 150, 800) is created and configured for the communication hub (20), or when an existing processing component (100, 102, 104, 150, 800) has been moved to a new physical location or a new network location.

A connection request may be received (block 300) by the communication hub (20) from a user device (108). The connection request may identify a component (100, 102, 104, 150, 800) for which network communication needs to be established, or may identify a component (100, 102, 104, 150, 800) for which network communication has previously been established that needs to be modified or re-established. The communication hub (20) may identify the component (100, 102, 104, 150, 800) type based upon the received (block 300) request, and display (block 302) connection instructions and input options that are specific to that component (100, 102, 104, 150, 800) via a display (606) of the user device (108). Information provided by a user in response to the connection instructions may be received (block 304) by the communication hub (20) and used to attempt (block 306) to establish a network connection between the communication hub (20) and the component (100, 102, 104, 150, 800).

If this network connection is successful, as may be indicated by a successful network ping, packet exchange, or other transmission of information, a success message may be displayed (block 310) indicating that the component (100, 102, 104, 150, 800) connection was successful. If the network connection was not successful, perhaps due to user error or a network issue, a connection failure message may be displayed (block 312) and the user may be returned to a step where the connection instructions are displayed (block 302) so that further attempts may be made.

Figure 28:
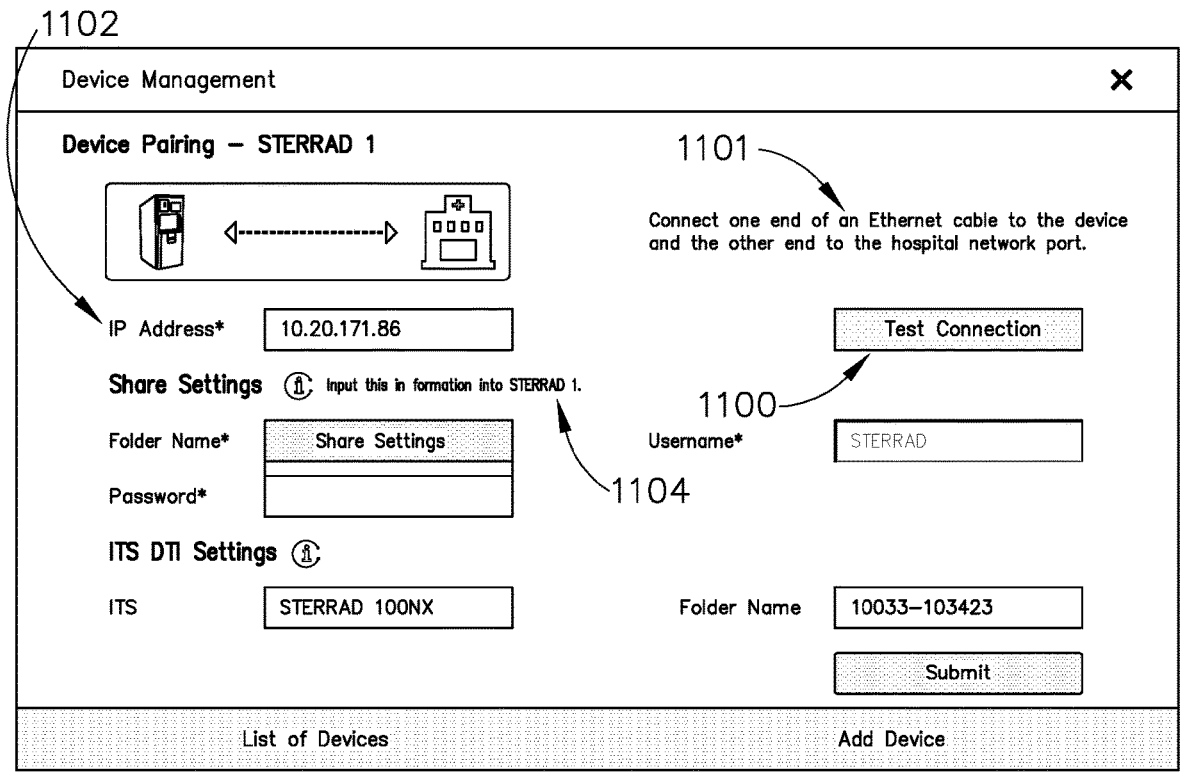
FIG. 28 shows an example of an interface that may be used to provide guidance to a user while adding a medical device processing component to a network via a user device coupled with the communication hub of FIG. 7 or directly via the communication hub of FIG. 8.
Figure 29:
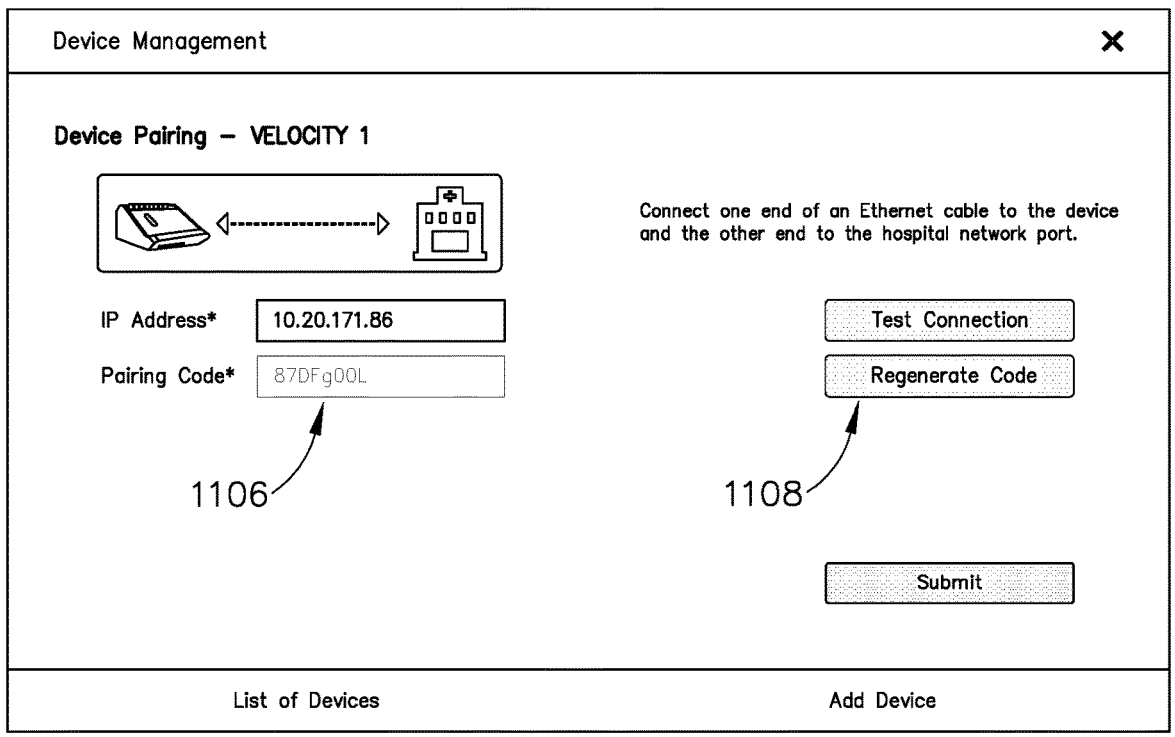
FIG. 29 shows an example of an interface that may be used to provide guidance to a user while adding a medical device processing component to a network via a user device coupled with the communication hub of FIG. 7 or directly via the communication hub of FIG. 8.

FIGS. 28-29 show several examples of interfaces that may be displayed to a user as part of the steps of FIG. 10. It should be understood that the interfaces of FIGS. 28-29 may be shown on a display of user device (108). In addition, or in the alternative, in cases where communication hub (20) has its own display (606), the interfaces of FIGS. 28-29 may be shown on display (606) of communication hub (20).

FIG. 28 shows an example of an interface that may be displayed to a user when displaying (block 302) connection instructions (1101, 1104) to a user. Such an interface may also have a network identifier (1102) where a unique identifier for a device may be provided, which may include an IP address, a MAC address, a proprietary addressing identifier, or other identifier. Also included may be an interface element that may be interacted with in order to test a connection (1100) before submitting the connection information. Interacting with a test connection (1100) tool may cause the communication hub (20) to send a test ping, packet, or communication to the identified device (1102) and report whether it was successfully received. An interface may be displayed to a user when displaying (block 310) connection success after a successful (block 308) device connection attempt (block 306).

FIG. 29 shows an alternate exemplary interface that may be used to display (block 302) connection instructions to a user. The interface of FIG. 29 shows additional features that a device connection interface may have, such as a dynamically generated code (1106) that may be generated by either the communication hub (20) or the connecting component (100, 102, 104, 150, 800), and then provided to the other component (100, 102, 104, 150, 800) which may use the code to locate and connect to the component (100, 102, 104, 150, 800) via the network. For example, in some versions, the communication hub (20) is configured to generate a connection code by interacting with an interface element (1108) to cause a connection code (1106) to be displayed. The connection code (1106) may then be entered via an interface of the target component (100, 102, 104, 150, 800), such as a sterilizing cabinet (100) or indicator analyzer (102) keyboard or touch screen, which is able to determine the communication hub (20) network identity and location based upon the code. The target component (100, 102, 104, 150, 800) may send a test communication to the communication hub (20) that, when received, may be used by the communication hub (20) to identify the network identity and location of the target device.

An alternate exemplary interface may be used to display (block 302) connection instructions to a user, as well as a username and password requirement that may be required in addition to identifying the target component (100, 102, 104, 150, 800), which may be useful when connecting to devices (100, 102, 104, 150, 800) that store sensitive medical information and which must be protected with some level of authentication. Other alternate examples of interfaces may be used to display (block 310) a success message after a successful (block 308) connection attempt (block 306).

In addition to using generated codes that may be decrypted or interpreted in order to identify a component (100, 102, 104, 150, 800) within a network for connection and unique identifiers such as IP address or MAC address, other methods exist that may be used to help connect or pair devices (100, 102, 104, 150, 800) with communication hub (20). For example, using an alternate input (614) such as a barcode or QR code scanner, or a mobile device camera configured to capture an image of a barcode or QR code, or a wireless technology such as NFC or RFID, device connection may be completed between a communication hub (20) and a target component (100, 102, 104, 150, 800). For example, one or both devices (100, 102, 104, 150, 800) could have or display a physical tag with a visual identifier or a wireless tag with a unique identifier, and such information may be captured by a user device (108) with an alternate input (614) and used to complete the connection. This could also include, for example, a sterilizing cabinet (100) having a QR code or NFC tag that, when scanned, automatically populates and submits network identifier information to complete the connection. Such a tag could be physically placed on the equipment, or could be displayed via a display of the equipment, or transmitted via a wireless communication transmitter of the equipment. Such a machine readable code, once read, could provide the information needed to complete the connection, or could provide instructions to retrieve the needed information from another location on the network such as a network identity server, which may contain one or more records identifying various devices on the network and what their current network location is. Variations on the steps and interfaces shown and discussed in relation to FIG. 10 exist, and will be apparent to those of ordinary skill in the art in light of the disclosure herein.

Figure 11:
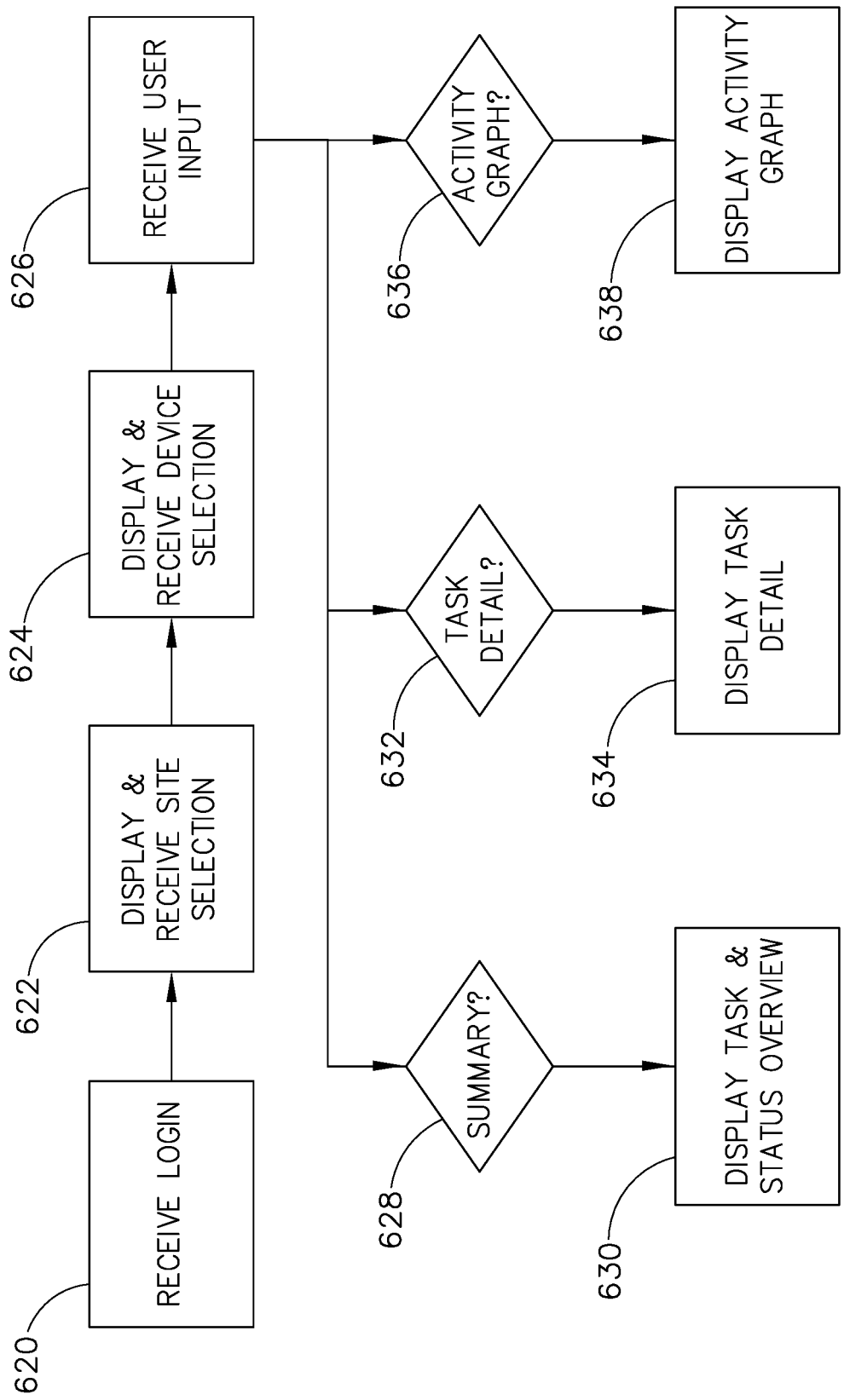
FIG. 11 shows an exemplary set of steps that may be performed using a communication hub, such as that shown in FIG. 7 or that shown in FIG. 8, to manage one or more medical device processing components.

FIG. 11 shows an exemplary set of steps that may be performed using a communication hub (20) such as that shown in FIGS. 7-8 to manage one or more processing components (100, 102, 104, 150, 800). Initially, the communication hub (20) may receive (block 620) a user's login information such as password and username from a user device (108). While not required, a user login may provide additional security that may be desirable before allowing a user to access a system that displays medical records and information. One or more sites may also be displayed to a user, and a site selection received (block 622) identifying a particular site or sites that a user wishes to monitor and manage processing components (100, 102, 104, 150, 800) at. A site may be a geographical location such as a hospital, or may be a particular location within a hospital, such that a hospital may have a single site or multiple sites. A site may have one or more communication hubs (20) providing connectivity and monitoring of processing components (100, 102, 104, 150, 800) at that site.

Once a site is specified, one or more devices (100, 102, 104, 150, 800) may be displayed to a user, and a component (100, 102, 104, 150, 800) selection may be received (block 624) identifying a particular component (100, 102, 104, 150, 800) or devices (100, 102, 104, 150, 800) that the user wishes to monitor or manage. Once one or more devices (100, 102, 104, 150, 800) have been selected to view or manage, the communication hub (20) may receive (block 626) user input from the user device (108) requesting summary information (block 628) for a device or devices, task details (block 632) for one or more tasks presently or previously performed on a component (100, 102, 104, 150, 800), or an activity graph (block 636) or other visualization of tasks presently or previously performed on a component (100, 102, 104, 150, 800). In response to received (block 626) requests, the communication hub (20) may transmit information to the user device (108) configured to cause the user device (108) to display (block 630) an overview of task information for one or more devices (100, 102, 104, 150, 800), display (block 634) detailed information for a task, or display (block 638) a visualization of task information for a component (100, 102, 104, 150, 800).

Figure 14:
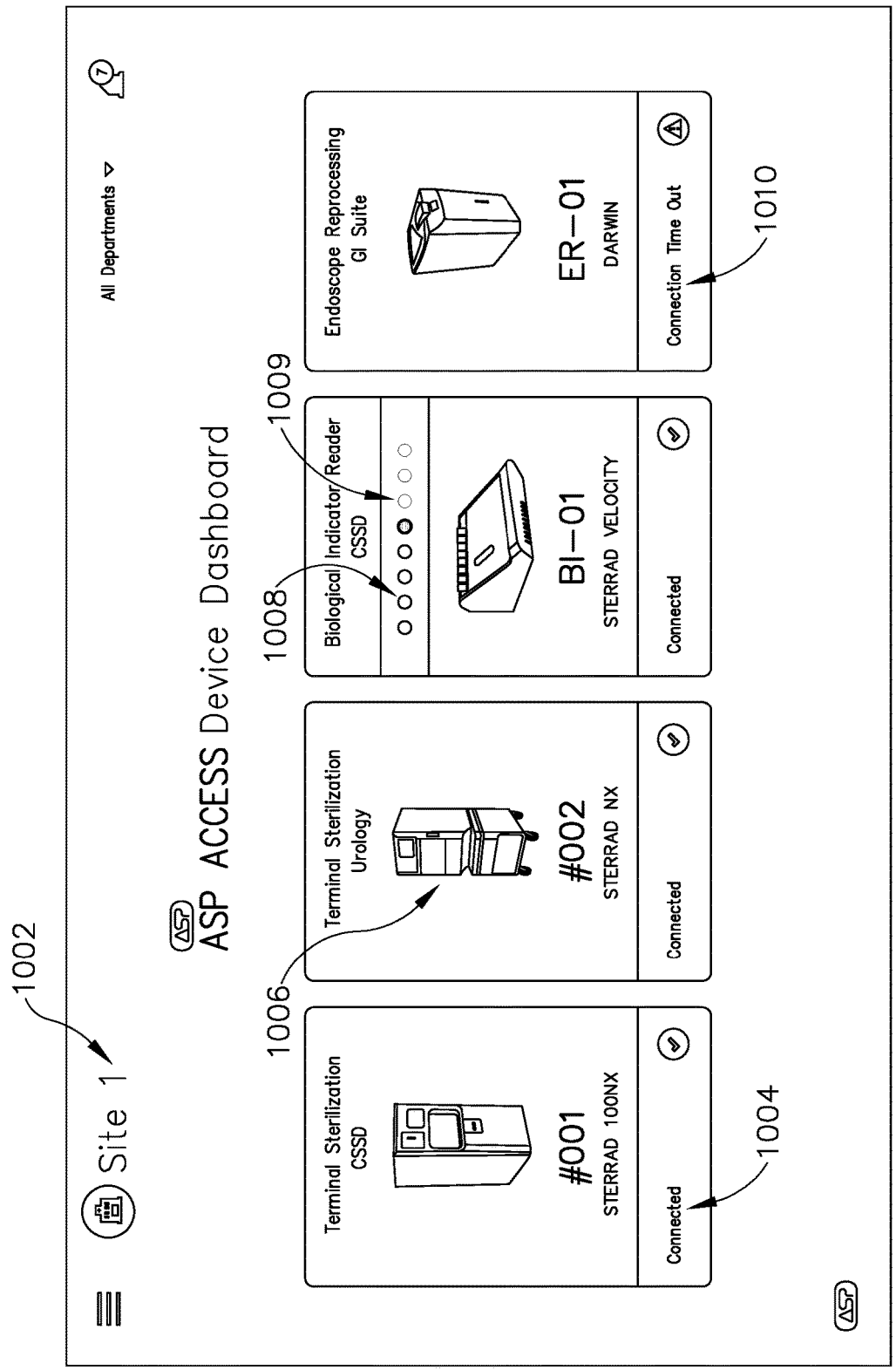
FIG. 14 shows an example of an interface that may be used to select a medical device processing component via a user device coupled with the communication hub of FIG. 7 or directly via the communication hub of FIG. 8.

FIGS. 14-26 show several examples of interfaces that may be displayed to a user during one or more of the steps shown in FIG. 11. A hospital site selection interface may be displayed as part of displaying and receiving (block 622) a hospital site selection from a user. FIG. 14 shows a component (100, 102, 104, 150, 800) selection interface that may be displayed as part of displaying a receiving a device selection from a user. While the interface of FIG. 14 shows four devices (100, 102, 104, 150, 800), it should be understood that any number of devices may be supported by scaling the display, individual icons, or adding additional interface elements to allow scrolling or page navigation of icons.

A site identifier (1002) indicates the user's site selection. A device status indicator may show that the component (100, 102, 104, 150, 800) is connected to the communication hub (20), or that there is an issue with the device connection (1010). A device icon (1006) may show a visual representation of a device to aid in selecting a component (100, 102, 104, 150, 800). This may be helpful, for example, when a user is accessing the communication hub (20) via a user device (108) such as a mobile phone, and a user is physically present at a sterilization cabinet (100) and wishes to monitor and manage its performance. Such a visual icon (1006) may aid the user in identifying the correct component (100, 102, 104, 150, 800) to view and manage. Additional device specific status indicators may also be shown, such as a biological indicator well (810) status for an indicator analyzer (102, 800), which may show whether a particular indicator well (810) is currently in use (1008) or open for use (1009). Such a feature may allow a clinician that needs to analyze an indicator to identify and locate an indicator analyzer (102, 800) that has currently available well (810) capacity using a mobile user device (108) rather than by physically locating the indicator analyzer (102, 800) and visually confirming whether or not a well (810) is available.

Figure 15:
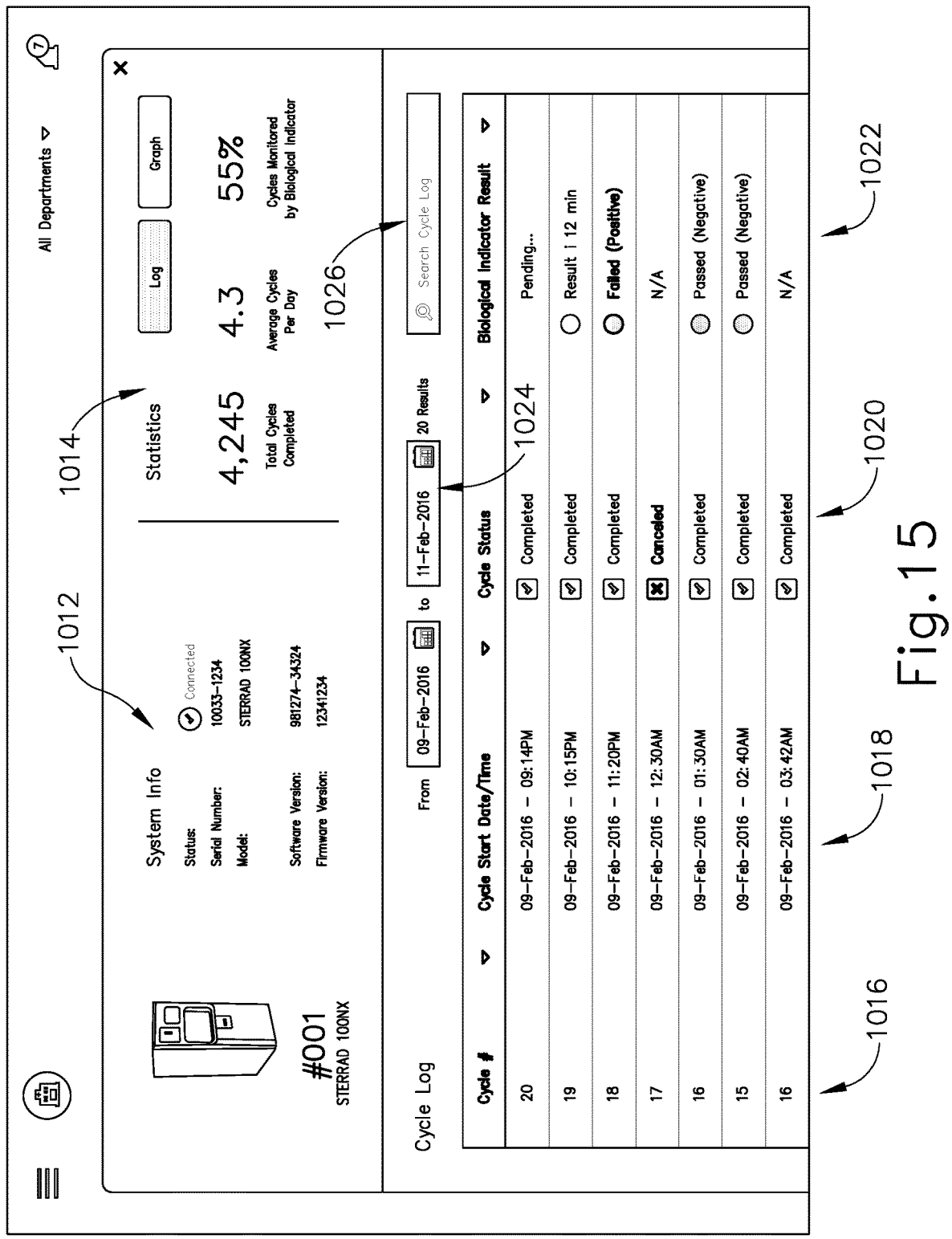
FIG. 15 shows an example of an interface that may be used to view information about a medical device processing component and its tasks via a user device coupled with the communication hub of FIG. 7 or directly via the communication hub of FIG. 8.

FIG. 15 shows an interface that may be displayed to a user as part of displaying (block 630) a task and status overview (1012) for a single component (100, 102, 104, 150, 800) to a user. Information shown may include a device identifier and icon, a statistics summary (1014) showing information such as how many sterilization cycles a sterilizing cabinet (100, 150) has completed, a number of cycles run per day, and a number of sterilization cycles in which a biological indicator has been used. Also shown may be a table having a row for each sterilization cycle performed, which may include columns such as a cycle identifier (1016), a cycle start time (1018), a cycle status (1020) indicating whether the cycle completed, failed, or was canceled, and a biological indicator result (1022) indicating whether an indicator was used, and whether the indicator determined that the sterilization cycle was a success or a failure. Also present on such an interface may sorting or filtering options, allowing a table to be sorted according to one or more of the columns, a date range selection (1024) allowing cycles present in the table to be restricted to a certain date range, and a cycle search (1026) allowing for a particular cycle number, date, status, or indicator result to be searched for.

Figure 16:
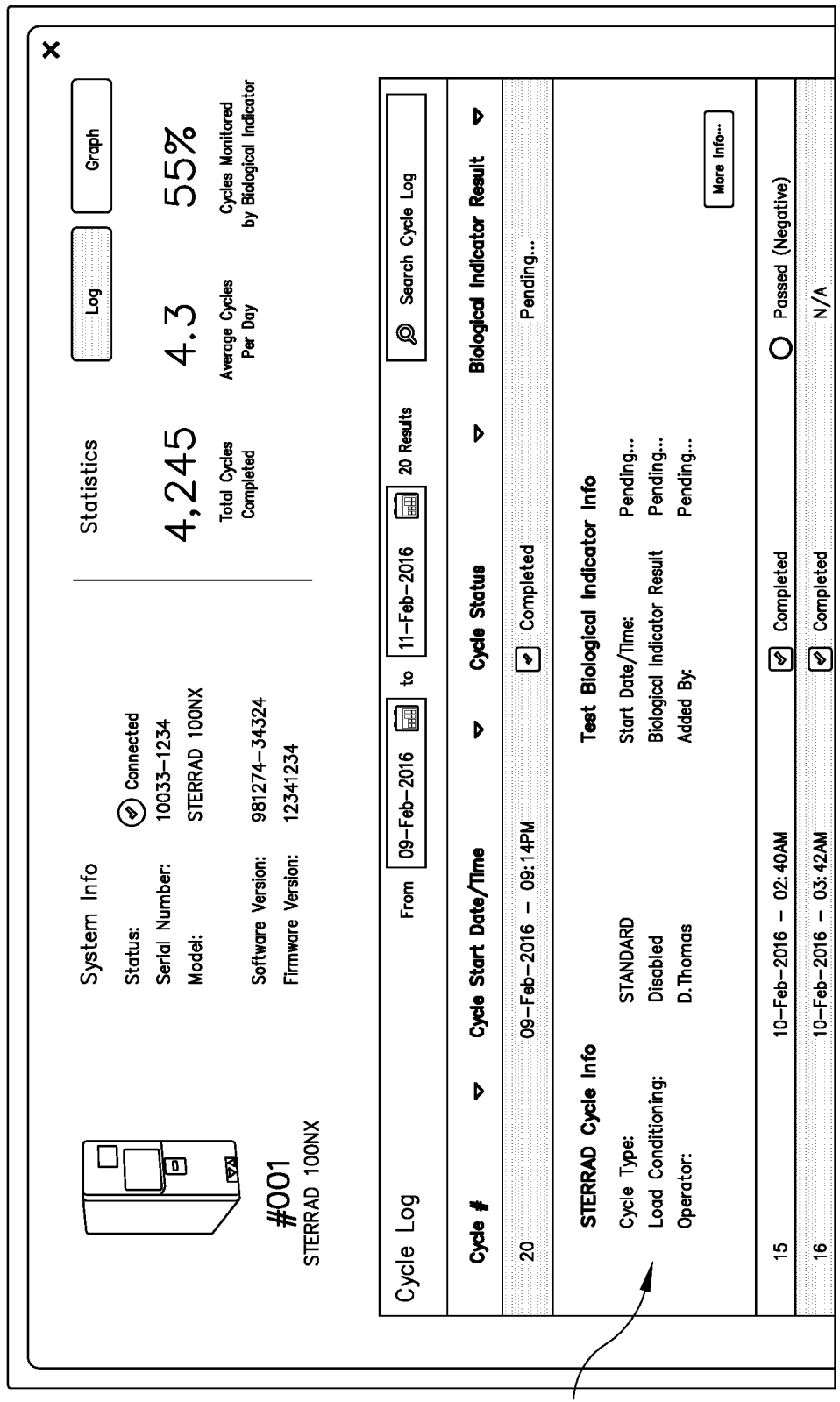
FIG. 16 shows an example of an interface that may be used to view additional information on a medical device processing component's tasks via a user device coupled with the communication hub of FIG. 7 or directly via the communication hub of FIG. 8.

FIG. 16 shows an interface similar to that of FIG. 15, where the results of a particular task have been expanded to show additional information (1030) relating to that cycle, which may include, for example, cycle type, load conditioning, cycle operator, start time, indicator result, and indicator operator. FIG. 16 may be shown as part of displaying (block 634) task detail for a particular task or cycle. FIG. 17 shows an additional interface that may be displayed to a user as part of displaying (block 634) task detail for a particular task. An interface such as that of FIG. 17 may show such information as a cycle information window (1032) having such information as cycle status, device identifier, cycle identifier, cycle type, load conditioning, cycle operator, cycle date, start time, end time, duration of cycle, facility name, department name, sterilization cassette lot number, biological indicator status, and manually entered cycle notes. Information shown may also include a biological indicator window (1034), that may show such information as indicator result, indicator reader used, indicator type, indicator lot number, indicator serial number, indicator expiration date, indicator operator, indicator entry time, indicator entry date, indicator result time, indicator color change, and incubation temperature.

Another interface may be shown as part of displaying (block 634) task detail for a particular cycle or device, which may include information such as maximum and minimum values for various physical attributes of sterilizing cabinet (100, 150) such as chamber, vapor, and conditioning pressure and temperature, delivered power, plasma time, and other attributes.

Figure 18:
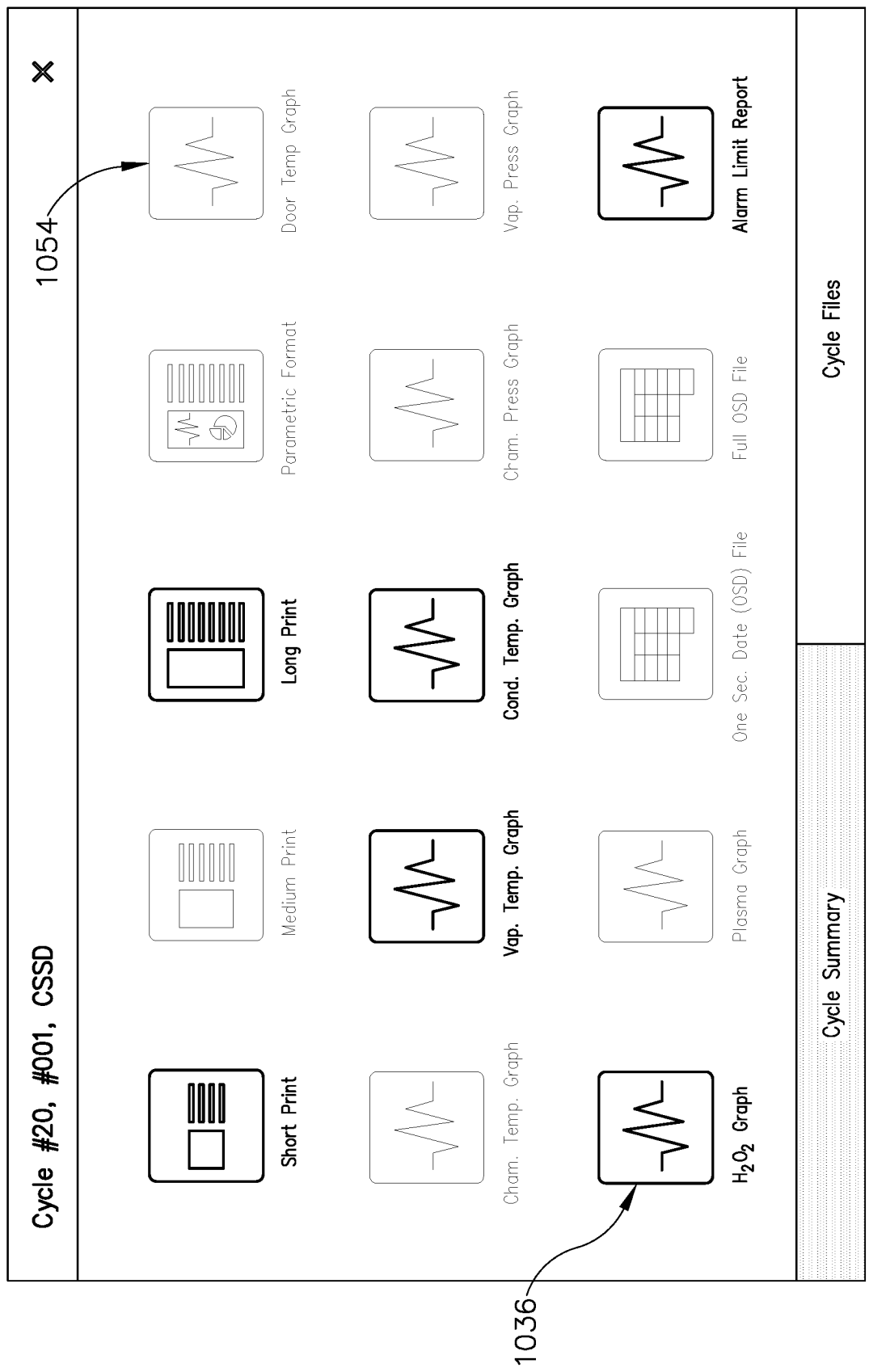
FIG. 18 shows an example of an interface that may be used to select to view information from a medical device processing component in one or more forms via a user device coupled with the communication hub of FIG. 7 or directly via the communication hub of FIG. 8.
Figure 24:
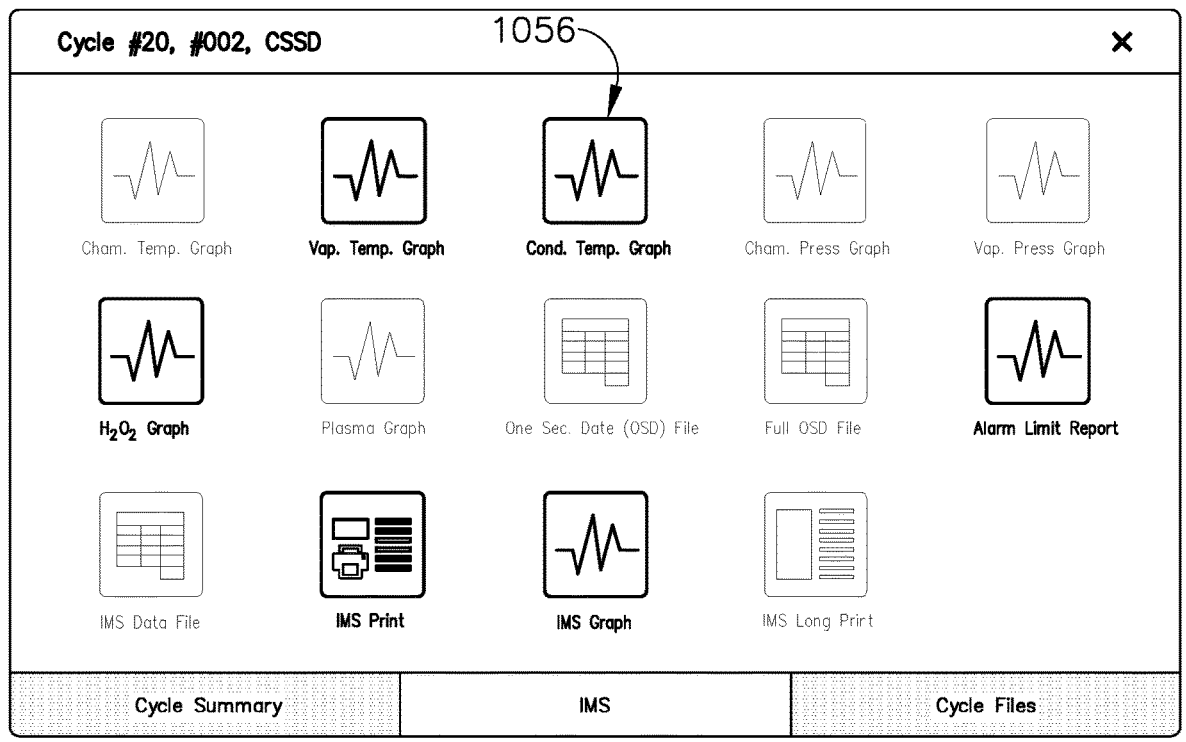
FIG. 24 shows an example of an interface that may be used to select to view information from a medical device processing component in one or more graphical views via a user device coupled with the communication hub of FIG. 7 or directly via the communication hub of FIG. 8.

FIG. 18 shows an interface that may be shown as part of displaying (block 638) a task or activity graph selection for a selected component (100, 102, 104, 150, 800). In such an interface, some icons may be solid (1036) indicating that they are available for the selected component (100, 102, 104, 150, 800); while others may be greyed out or semi-translucent (1054) indicating that they are unavailable for the selected component (100, 102, 104, 150, 800). For example, one type of sterilizing cabinet (100) may generate information during a sterilization cycle which can be viewed in an H2O2 graph (1036), but may not generate information which can be viewed in a door temperature graph (1054). FIG. 24 shows an interface that may be displayed for a different type of sterilizing cabinet (100), which supports some additional visualization options such a load conditioning temperature graph (1056).

Visualizations options may vary depending upon the particular device selected, but may include information relating to the device or a cycle of the device as a short printable view, medium printable view, long printable view, parametric format view, door temperature graph, sterilization chamber graph, vapor temperature graph, conditioning temperature graph, chamber pressure graph, vapor pressure graph, H2O2 graph, plasma graph, partial or complete one second data file, alarm limit report view, indicator data file, indicator printable view, indicator graphs, indicator long printable view, and other views and visualizations that may be desirable.

Figure 19:
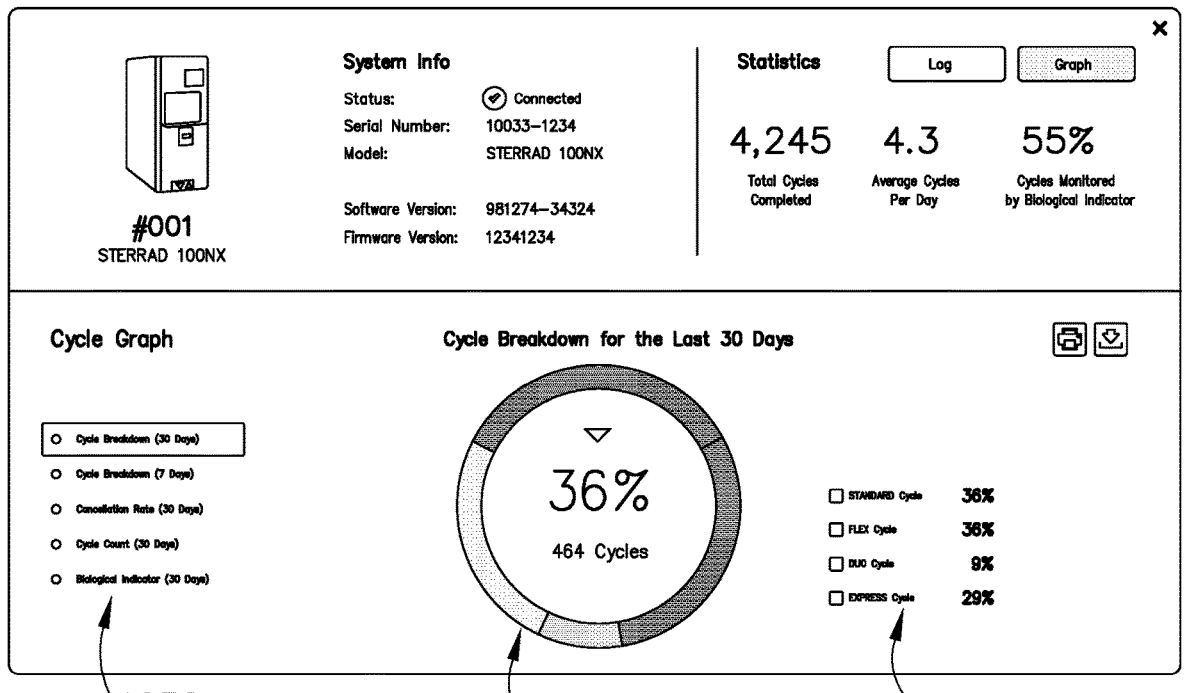
FIG. 19 shows an example of an interface that may be used to view information from a medical device processing component in a graphical form via a user device coupled with the communication hub of FIG. 7 or directly via the communication hub of FIG. 8.

FIG. 19 shows an interface that may be shown as part of displaying (block 638) a task or activity graph for a component (100, 102, 104, 150, 800). A graph type selection (1038) may be interacted with by a user to select to see information graphed as, for example, a 30-day cycle breakdown, a 7-day cycle breakdown, a 30-day cycle cancellation rate, a 30-day cycle count, a 30-day biological indicator usage, and other graphs as may be desirable for a sterilizing cabinet (100) or indicator analyzer (102). Also included may be a graphical visualization (1040) such as a chart, graph, table, or other data model that may include one or more visible data indicators such as size, shape, color, numbers, and arrangement, and a visualization key (1042) providing further explanation for graphical visualization (1040) including an indication of what visible data indicators represent.

Figure 20:
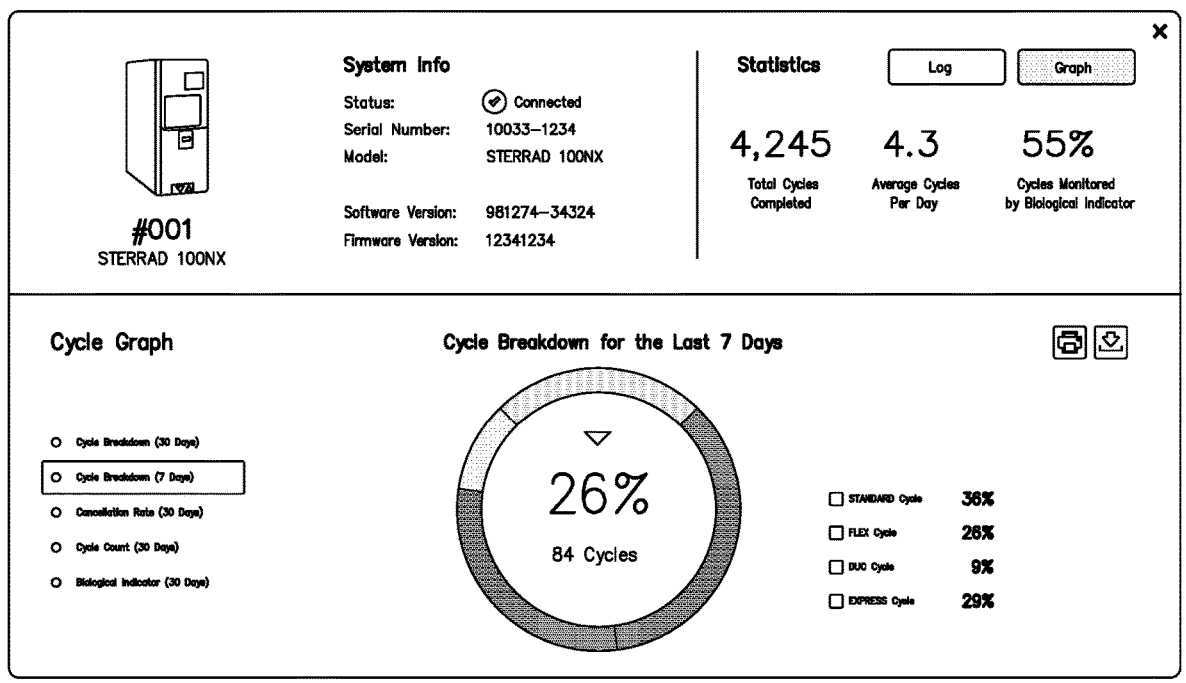
FIG. 20 shows an example of an interface that may be used to view information from a medical device processing component in an alternate graphical form via a user device coupled with the communication hub of FIG. 7 or directly via the communication hub of FIG. 8.
Figure 21:
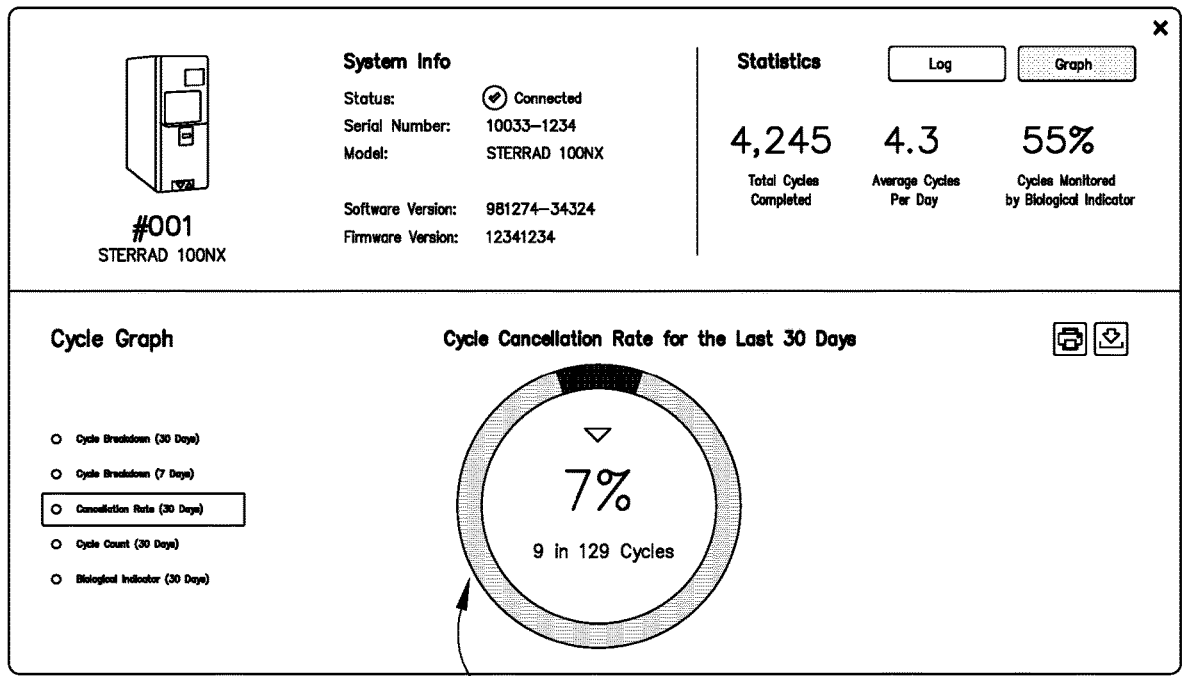
FIG. 21 shows an example of an interface that may be used to view failed task information from a medical device processing component in a graphical form via a user device coupled with the communication hub of FIG. 7 or directly via the communication hub of FIG. 8.
Figure 22:
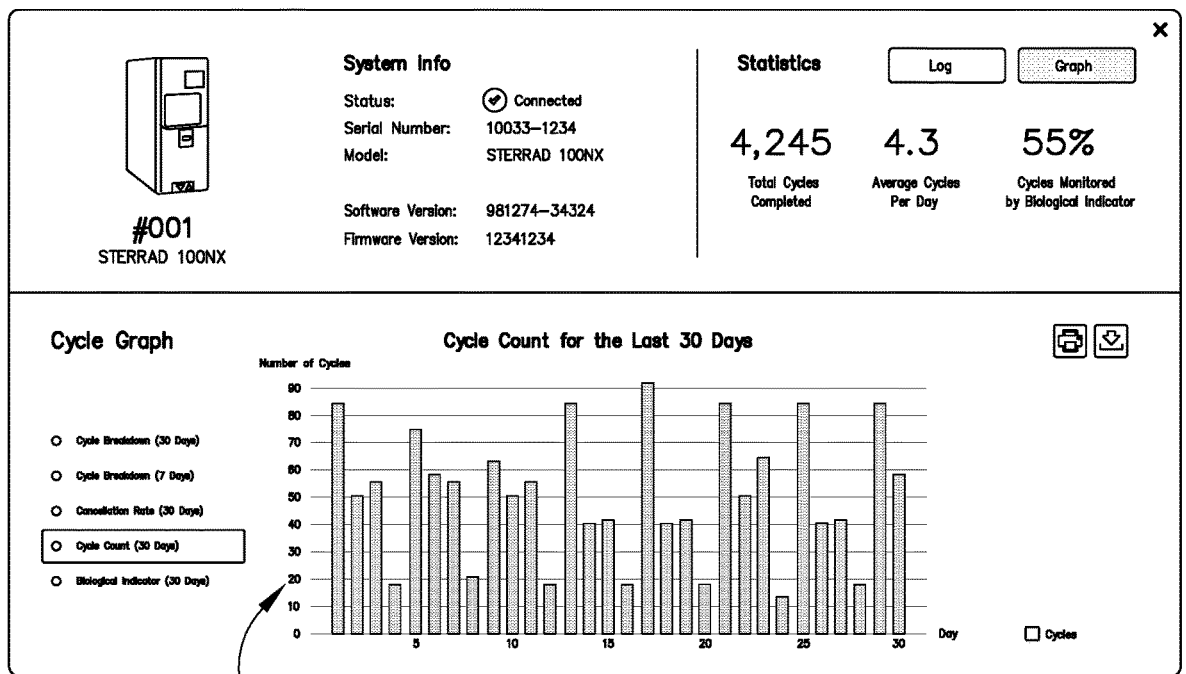
FIG. 22 shows an example of an interface that may be used to view information from a medical device processing component in yet another alternate graphical form via a user device coupled with the communication hub of FIG. 7 or directly via the communication hub of FIG. 8.
Figure 23:
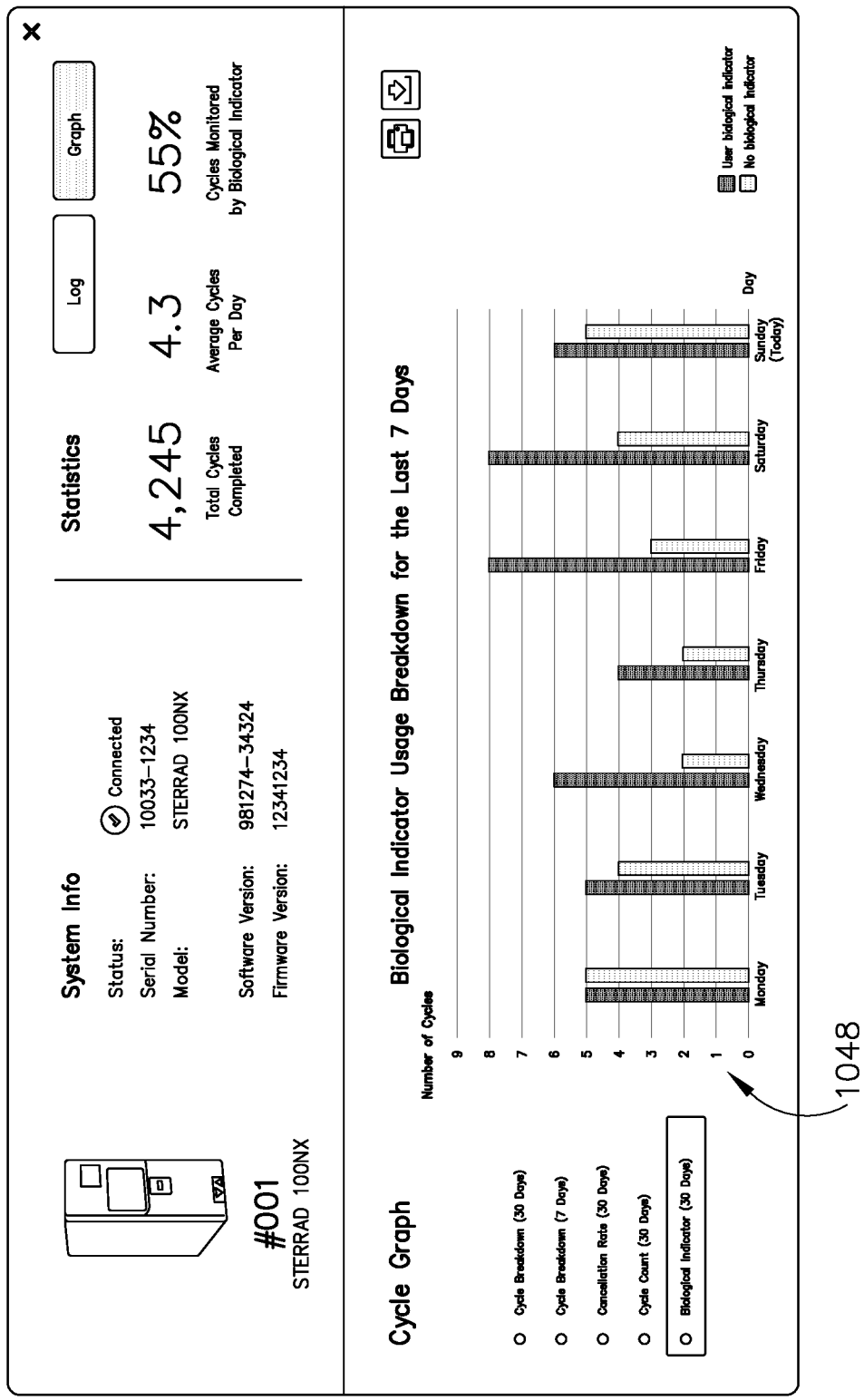
FIG. 23 shows an example of an interface that may be used to view information from a medical device processing component in yet another alternate graphical form via a user device coupled with the communication hub of FIG. 7 or directly via the communication hub of FIG. 8.

FIG. 20 shows an interface similar to that of FIG. 19, which may be shown after a user has selected to view a different cycle breakdown, such as the 7-day cycle breakdown instead of the 30-day cycle breakdown. FIG. 21 shows an interface similar to that of FIG. 19, which may be shown after a user has selected to view a cycle cancellation rate, and which may include a cancellation graph (1044) or other visualization showing a number of percentage of cycles which have been canceled or otherwise failed over the selected time period. FIG. 22 shows an interface similar to that of FIG. 19, which visualizes data as a bar chart (1046) instead of a pie chart. FIG. 23 shows an interface to that of FIG. 22, which visualizes data as a bar chart (1048) including two variables, one for cycles in which a biological indicator was used, and one for cycles which did not use a biological indicator.

Figure 25:
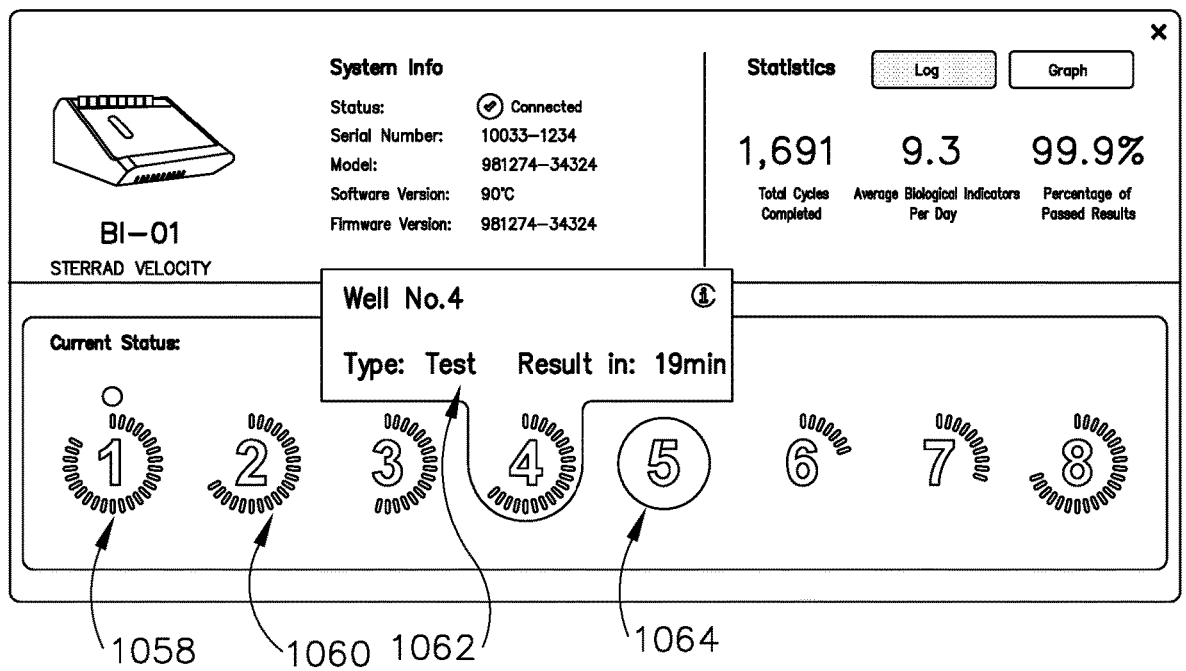
FIG. 25 shows an example of an interface that may be used to view and manage an indicator analyzer's tasks and information via a user device coupled with the communication hub of FIG. 7 or directly via the communication hub of FIG. 8.

FIG. 25 shows an interface that may be shown as part of displaying (block 630) a task or device overview or summary which shows additional status information for the selected device. FIG. 25 shows a status overview for an indicator analyzer (102, 800) that indicates whether each indicator well (810) is in use or not. While FIG. 25 shows such features specific to a biological indicator, it should be apparent that such principles may also be applied to other processing components (100, 102, 104, 150, 800) such as a sterilizing cabinet (100). An interface such as that shown in FIG. 25 may include an indicator well identifier (1058), an indicator well progress indicator (1060), an indicator well type (1062) and result for a selected indicator well (810), an indicator well vacant indicator (1064), and other information that may be generated by the indicator analyzer (102, 800) and displayed on a status overview interface. Similar information may be shown for a sterilization cabinet (100, 150), such as how many chambers (152) the cabinet (100, 150) has, which chambers (152) are in use, what their current temperature or pressure is, a remaining time for a currently performed cycle, and other information that may be generated by a sterilizing cabinet (100, 150) and displayed on a status overview interface.

Another interface may show a table of task details for an indicator analyzer (102, 800). Shown information may include an analysis start time, biological indicator type, biological indicator status, sterilization cycle number, sterilization cycle type, and sterilization cycle status. Also shown may be an indicator well status that indicates the status of each indicator well (810) of an indicator analyzer (102, 800). FIG. 26 shows an interface which may be shown when a user selects a particular task from the table in order to see additional information for that task or indicator analysis.

Another interface may be shown when a user selects to see a complete set of information for an indicator task and any related sterilization cycle task (1032). This interface may display information including but not limited to whether the biological indicator passed the analysis, the identity of the indicator analyzer (102, 800), the type of biological indicator, the lot number of the biological indicator, the serial number of the biological indicator, the expiration date of the biological indicator, the date and time of the biological indicator analysis, the identity of the operator who initiated the biological indicator analysis, the temperature at which the biological indicator analysis was carried out, the identity of the sterilizing cabinet (100, 150) in which the biological indicator encountered a sterilization cycle, the associated sterilization cycle number, the type of associated sterilization cycle, the identity of the operator of the associated sterilizing cabinet (100, 150), the time and location of the associated sterilization cycle, etc.

Another interface may be shown as part of displaying (block 630) a task or device overview, specifically, when there is a history of notifications for the task or component (100, 102, 104, 150, 800). Such an interface may show a notification table having a notification type, which may include notification types such as cancelled cycle, failed (positive) biological indicator, passed (negative) biological indicator, and other notifications. Such a table may additionally show a details column which may provide details relating to the notification, such as any error messages or status reports generated as part of the notification.

Another interface may be shown as part of displaying (block 630) a task or device overview, specifically, when there may be user entered notes associated with the component (100, 102, 104, 150, 800) or task. Information shown may include a date of note entry, note author, and note text. An interface may be shown as part of displaying (block 630) a task or device overview for an indicator analyzer (102) that includes information on biological indicator lots. Information shown may include a lot identifier, a control result for that lot, a previous control end time, and a number of controls performed for that lot. Such an interface may be helpful in providing information to a user to identify biological indicator lots from which to select an indicator for a test, and may also aid in selecting an indicator from a let for a control so that others may use indicators from that lot for tests.

Figure 12:
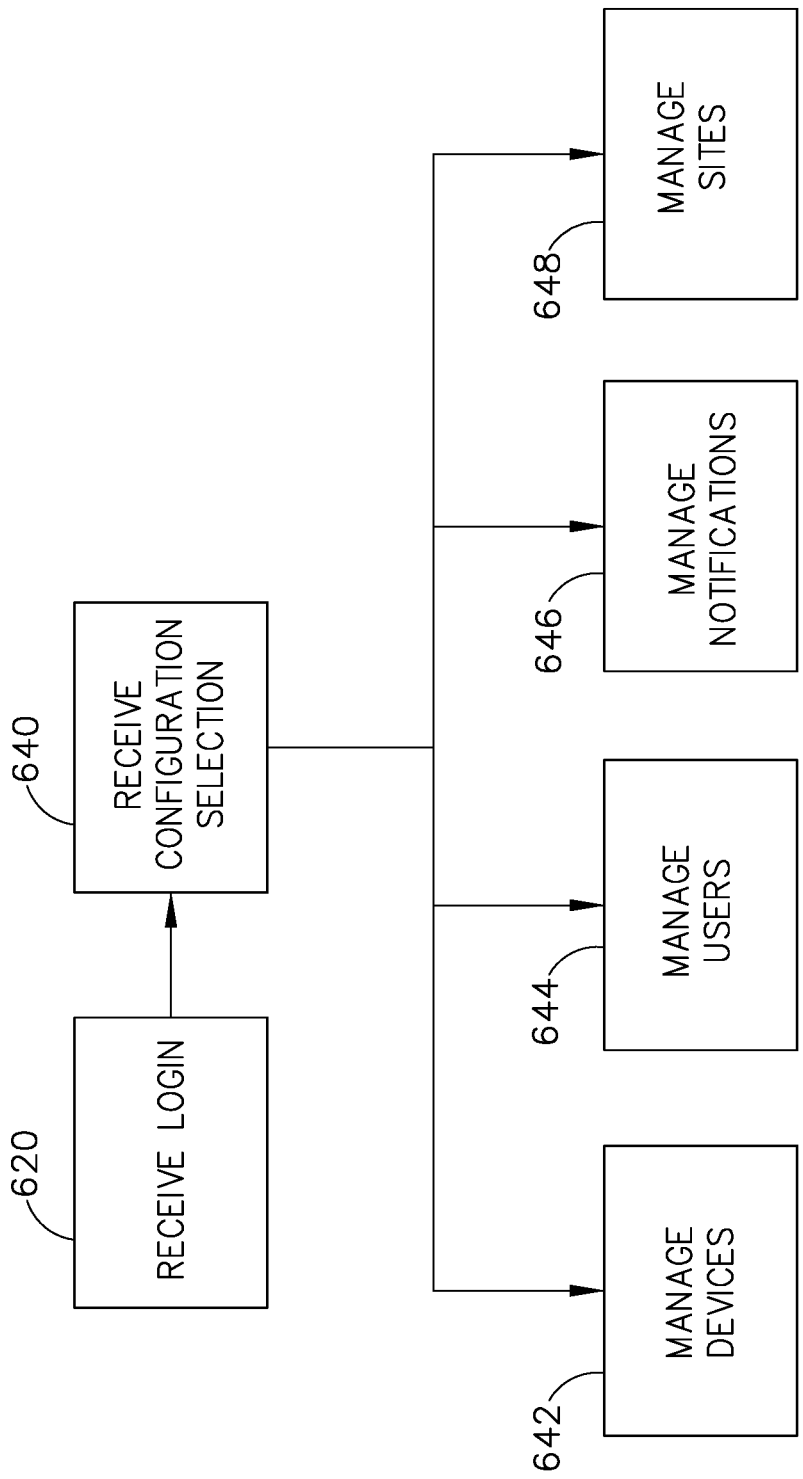
FIG. 12 shows an exemplary set of steps that may be performed using a communication hub, such as that shown in FIG. 7 or that shown in FIG. 8, to manage configurations of a network of medical device processing components.

FIG. 12 shows an exemplary set of steps that may be performed using a communication hub (20) such as that shown in FIGS. 7-8 to manage configurations of a network of processing components (100, 102, 104, 150, 800). After a login attempt is received (block 620) and validated, one or more configuration selections may be received (block 640) from a user of the user device (108). Received configuration selections may include selections to manage devices (block 642) that are configured to be monitored or managed by the communication hub (20), selections to manage users (block 644) that are configured to access or interact with the communication hub (20), selections to manage notification settings (block 646), settings to manage sites that are monitored and managed by the communication hub (20), and other similar configurations. Managing devices (block 642) may include adding, removing, or modifying configured devices (100, 102, 104, 150, 800), and may also include connecting to devices (100, 102, 104, 150, 800) over a network as described in FIG. 10. Managing users (block 644) may include adding, removing, or modifying users. Managing notifications may include configuring and modifying notification settings, such as determining which users will receive certain notification types and over what method of communication they will be received. Managing sites may include adding, removing, or modifying sites, and determining what users and devices (100, 102, 104, 150, 800) are associated with sites.

Another interface may be shown when a user manages devices (block 642). Information shown may include a table having one or more of a device identifier, a device category, a device department, and a device connection status. FIG. 27 shows an interface that may be shown when a user manages devices (block 642) and selects a particular component (100, 102, 104, 150, 800) to manage, modify, or review. Shown information may include additional device information (1098) such as serial number, model number, software version, firmware version, and cycle types or other tasks supported by the component (100, 102, 104, 150, 800). Another interface may be shown when a user selects to modify a component (100, 102, 104, 150, 800). Information that is displayed and modifiable by a user interacting with such an interface may include device identifier, device category, device model, cycle types, tasks, or other features supported by the device, device department, serial number, software version, firmware version, and language.

Another interface may be shown when a user selects to disable a component (100, 102, 104, 150, 800) during device management (block 642), requesting the user to explicitly confirm their intent to disable component (100, 102, 104, 150, 800). Another interface may also be shown when a user selects to add a component (100, 102, 104, 150, 800) during device management (block 642). Information that is shown and modifiable by a user when adding a component (100, 102, 104, 150, 800) may include device identification, device category, device model, cycle, tasks, or features supported by the device, department, serial number, software version, firmware version, and device language. One or more pieces of device information may be automatically populated or updated by connecting the communication hub (20) to a component (100, 102, 104, 150, 800), which may then provide information over the network. Another interface may be shown to a user during device management (block 642) when a component (100, 102, 104, 150, 800) is created but not yet connected to the communication hub (20), which may allow a user to proceed to the steps of FIG. 10 and the interfaces of FIGS. 28-29 with a single interaction.

Another interface may be shown to a user as part of user management (block 644). Such an interface may show and allow modifications to a user information table (1110) that may include such information as first and last names of users, user types, usernames, and email addresses for one or more users that have been configured within the system.

Another interface may be shown to a user as part of site management (block 648). Such an interface may show and allow modifications to a site information table (1112) that may include such information as customer identifier, site name, country, states, and city. An interface may be shown to a user as part of site management (block 648). Such an interface may show information on one or more sites, and allow a user to select sites (1114) to activate or deactivate. An interface may be shown to a user as part of site management (block 648) when a user selects to add a new site. Information that is shown and modifiable by a user may include customer identifier, site name, stress address, city, state, country, zip code, global region, cluster, biomed, phone number, and primary, secondary, and tertiary FSE.

Another interface may be shown to a user as part of notification management (block 646). Such an interface may show a notification configuration window (1116) which allows a user to select, for each notification type, whether notifications should be generated through one or more communication types such as email, SMS, web portal, phone, or other similar communications. Another interface may be shown to a user as part of notification management (block 646) when a user selects to view a summary of many notifications for a particular site or communication hub (20). Such an interface may show notifications from a variety of devices (100, 102, 104, 150, 800) for that site or hub (20), and information may include notification type and description (1118), origin device identifier (1120), and date and time of notification receipt (1122).

Figure 13:
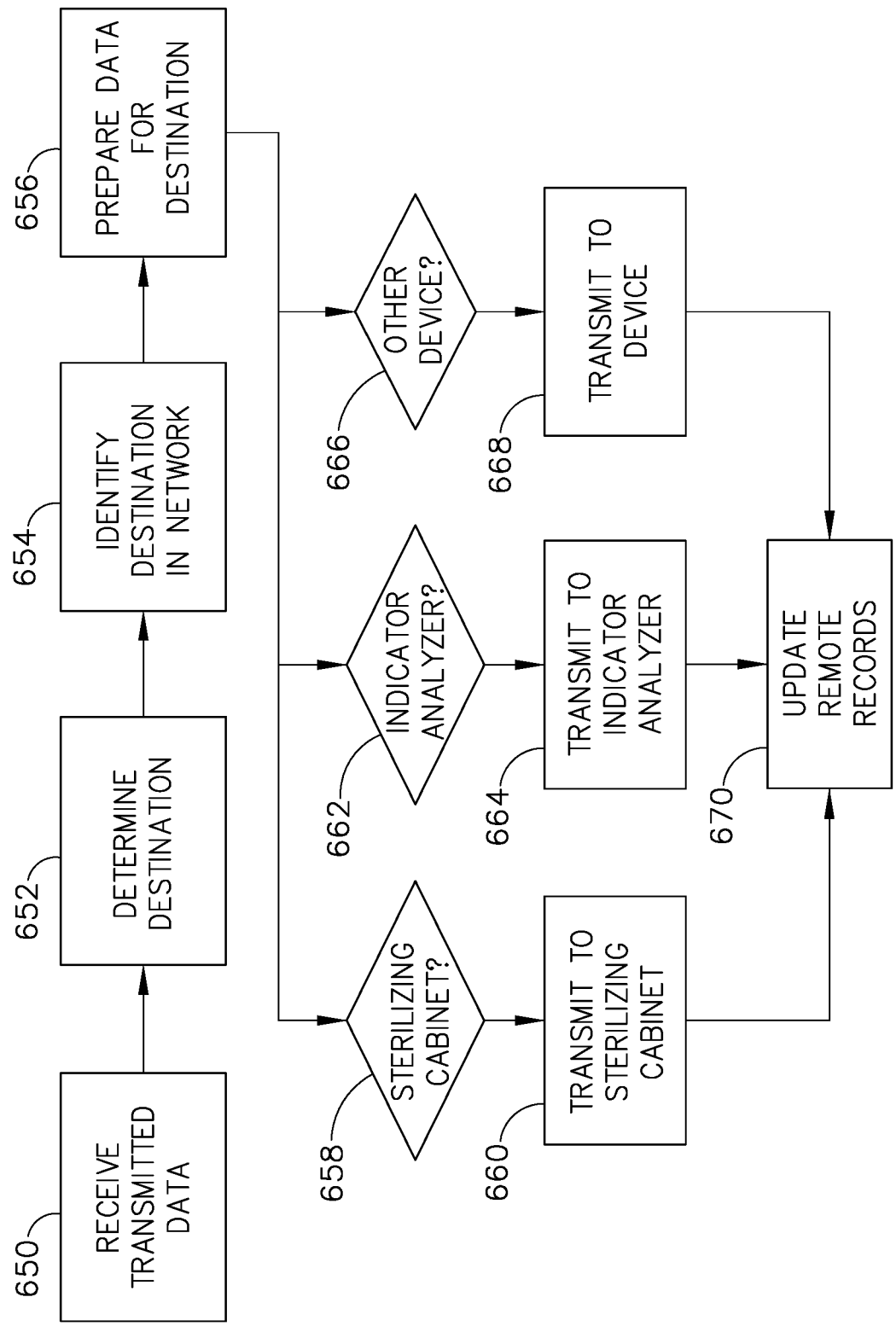
FIG. 13 shows an exemplary set of steps that may be performed using a communication hub, such as that shown in FIG. 7 or that shown in FIG. 8, to manage communications within a network of medical device processing components.

Another interface may be shown to a user as part of notification management (block 646) when a user selects to view additional information for a single notification. Such additional information may include, for example, indicator test result, indicator test type, lot number, time indicator added, device identifier, cycle type, cycle identifier, cycle start time, and cycle end time. Additional information shown may include, for example, device last connection time, device last connection site, device current connection status, and other similar information FIG. 13 shows an exemplary set of steps that may be performed using a communication hub (20) such as that shown in FIG. 7-8 to manage communications between devices (100, 102, 104, 150, 800) of a network of processing components (100, 102, 104, 150, 800). In some cases, devices present in a network of processing components (100, 102, 104, 150, 800) may exchange information with each other through communication hub (20). As has been disclosed above in some detail, this may include situations where an indicator analyzer (102) or sterilizing cabinet (100)

generates information which is passed to communication hub (20) and then accessed and displayed on a user device (108). However, this could also include a sterilizing cabinet (100) generating a record of a sterilization cycle, and transmitting that record to an indicator analyzer (102) so that a biological indicator analysis performed on the analyzer (102) may be associated with a sterilization cycle performed on the sterilizing cabinet (100). This could also include information generated by one or more devices (100, 102, 108, 150, 800) being transmitted to server (106) via the communication hub (20), such as medical records being generated at a device (100, 102, 108, 150, 800) and then sent to a server (106) for long term medical record storage. This could also include the opposite, such as software updates, firmware updates, user configurations, site configurations, device configurations, and other information being prepared on server (106) and distributed to one or more devices (100, 102, 108, 150, 800) where they can be used to update software, firmware, or configurations. Other communications and communication types enabled by a communication hub (20) connecting one or more processing components (100, 102, 104, 150, 800) will be apparent to those of ordinary skill in the art in light of the disclosure herein.

When a communication is received (block 650) by the hub (20), it may be determined (block 652) what the communications destination is based upon the type, form, or contents of data included in the communication. For example, if hub (20) receives a software patch bundled with data indicating it is intended for sterilization cabinets (100), the hub (20) will be able to determine the destination for the software patch. The hub (20) may also identify (block 654) one or more destinations within its network. Following the above example, this could include identifying each sterilization cabinet (100, 150) that the hub (20) is connected to across one or more configured sites. The hub (20) may also prepare (block 656) or modify the data in order to prepare it for transmission to the destination. This could include changing the form of the communication to a format that is expected or acceptable by the destination device, could include removing unnecessary information from the communication, such as destination identifying information which may no longer be necessary, could include encrypting the information, pairing it with authentication information, or modifying it in other ways to ensure security of the transmission to the destination, and other types of data preparation activities. The hub (20) may also then transmit data to one or more destinations depending upon whether the destination has been identified as a sterilizing cabinet (block 658, 100), indicator analyzer (block 662, 102), or another device (block 666) such as a user device (108) or server (106).

If the destination is identified as one or more sterilizing cabinets (block 658), the hub (20) may transmit the prepared data to the destination where it may be received and used to update software, update firmware, display a message via a display of the cabinet (100, 150), update one or more records stored locally on the cabinet (100, 150) such as user configurations or device configurations, or similar actions. In cases where data is sent to a sterilizing cabinet (block 660), it may also be sent to a server (106) where a remote record of the data may be maintained (block 670) in case of data loss or device failure. Similarly, if the target destination is determined to be one or more indicator analyzers (block 662) or other device (block 666), the prepared data may be sent to the analyzer (block 664) or other device (block 668) and also maintained as a remote record (block 670).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A processing component network comprising: (a) a communication hub comprising: (i) a processor, (ii) a memory, and (iii) a network interface; (b) a set of medical device processing components; and (c) a user device; wherein the processor is configured to execute instructions to cause the communication hub to: (i) receive a first set of device configurations from the user device, (ii) create a device record for a first medical device processing component of the set of medical device processing components based upon the first set of device configurations, (iii) establish a network connection to the first medical device processing component via the network interface, (iv) provide a first set of device information to the user device, wherein the first set of device information is received from the first medical device processing component, and (v) provide a task record to a second medical device processing component of the set of medical device processing components, wherein the task record describes a first task performed by the first medical device processing component; wherein the first set of device information is configured to cause the user device to display at least a portion of the first set of device information via a display of the user device, and wherein the task record is required by the second medical device processing component in order to perform a second task.

Example 2

The processing component network of Example 1, wherein the first medical device processing component comprises a sterilization chamber; wherein the second medical device processing component comprises a biological indicator analyzer; wherein the first task comprises a sterilization cycle performed in the sterilization chamber; and wherein the second task comprises an analysis of a biological indicator used in the first task.

Example 3

The processing component network of any one or more of Examples 1 through 2, wherein the network interface comprises a Wi-Fi transceiver; wherein the user device is selected from the group consisting of: a smartphone, a computer, a tablet, and a laptop; wherein the first set of device configurations comprises: (i) a site configuration, (ii) a device configuration, and (iii) a user configuration; wherein the first set of device information comprises five or more of: (i) a cycle identifier (ii) a device identifier, (iii) a cycle status, (iv) a biological indicator result, (v) a number of total cycles, (vi) a number of average cycles per day, (vii) a number of cycles including a biological indicator, (viii) a number of completed cycles, (ix) a number of total indicator analyses, (x) a number of indicator analyses per day, (xi) a number of indicators having a pass result, (xii) an indicator analyzer well status, (xiii) a biological indicator identifier, (xiv) a biological indicator lot number, and (xv) a biological indicator color change.

Example 4

The processing component network of any one or more of Examples 1 through 3, wherein the instructions to cause the communication hub to create a device record comprise instructions to: (i) determine a device identifier, a device model, and a device serial number based upon the first set of device configurations, (ii) associate the first medical device processing component with a site, wherein the site is associated with a geographic location, and (iii) associate a user with the site; and wherein the communication hub is further configured to only provide the first set of device information to the user device when the user device is associated with the user that is associated with the site.

Example 5

The processing component network of Example 4, wherein the processor is further configured to execute instructions to cause the communication hub to: (i) receive a notification from the first medical device processing component, (ii) determine a set of users that are associated with the site, the set of users including the user, and (iii) provide the notification to a set of user devices that are associated with the set of users.

Example 6

The processing component network of any one or more of Examples 1 through 5, wherein the instructions to cause the communication hub to establish a connection to the first medical device processing component comprise instructions to: (i) receive a device connection request from the user device, (ii) provide a connection interface to the user device, (iii) receive a set of device connection information from the user device, the set of device connection information received via the connection interface, and (iv) attempt a connection to the first medical device processing component using the set of device connection information; wherein the connection interface comprises a set of connection instructions.

Example 7

The processing component network of Example 6, wherein the connection interface is configured to receive, from the user device: (i) a network location identifier, a username, and a password, or (ii) a network pairing code.

Example 8

The processing component network of any one or more of Examples 1 through 7, wherein the first medical device processing component comprises a sterilizing cabinet, and wherein the instructions to provide the set of device information comprise instructions to provide a device overview interface to the user device, wherein the device overview interface comprises two or more of: (i) a device identifier, (ii) a sterilization cycle summary, (iii) a sterilization cycle table, or (iv) a sterilization cycle visualization.

Example 9

The processing component network of Example 8, wherein the sterilization cycle summary comprises a total number of cycles, an average cycles per day, and a number of cycles including a biological indicator; wherein the sterilization cycle table comprises a set of rows, each row corresponding to a single sterilization cycle performed by the sterilizing cabinet; and wherein the sterilization cycle visualization comprises one or more of a pie chart, a bar chart, or a graph.

Example 10

The processing component network of any one or more of Examples 1 through 9, wherein the first medical device processing component comprises a biological indicator analyzer, and wherein the instructions to provide the set of device information comprise instructions to provide a device overview interface to the user device, wherein the device overview interface comprises two or more of: (i) a device identifier, (ii) a biological indicator analysis summary, (iii) an indicator well status, or (iv) an indicator analysis table.

Example 11

The processing component network of Example 10, wherein the biological indicator analysis summary comprises a total number of analyses, a number of analyses per day, and a number of analyses indicating cycle success; wherein the indicator well status comprises a plurality of well indicators, each well descriptor comprising a vacancy indicator and an analyses duration indicator; and wherein the indicator analysis table comprises a set of rows, each row corresponding to a single biological indicator analysis performed by the biological indicator analyzer.

Example 12

A method for monitoring and managing a network of medical device processing components comprising the steps: (a) creating a site record; (b) creating a device record for a first medical device processing component and associating the device record with the site record; (c) connecting the first medical device processing component to a communication hub via a network interface of the communication hub; (d) receiving a site selection identifying the site record from a user device and, in response, providing a list of devices associated with the site record to the user device; (e) receiving a device selection identifying the device record from the user device and, in response, providing a set of device information associated with the first medical device processing component to the user device; (f) receiving, at the communication hub, a task record from the first medical device processing component, the task record describing a first task performed by the first medical device processing component; and (g) providing the task record to a second medical device processing component, wherein the second medical device processing component is configured to perform a second a second task based upon the task record.

Example 13

The method of Example 12, wherein the act of connecting the first medical device processing component to the communication hub comprises: (i) receiving a device connection request from the user device, (ii) causing the user device to display a connection interface, (iii) receiving a set of device connection information from the user device, and (iv) attempting a connection to the first medical device processing component using the set of device connection information; and wherein the connection interface comprises a set of connection instructions.

Example 14

The method of Example 13, wherein the connection interface is configured to provide to the communication hub: (i) a network location identifier, a username, and a password, or (ii) a network pairing code.

Example 15

The method of any one or more of Examples 12 through 14, wherein the first medical device processing component comprises a sterilizing cabinet, wherein providing the set of device information comprises causing a device overview interface to display on the user device, wherein the device overview interface comprises two or more of: (i) a device identifier, (ii) a sterilization cycle summary, (iii) a sterilization cycle table, and (iv) a sterilization cycle visualization.

Example 16

The method of Example 15, wherein the sterilization cycle summary comprises a total number of cycles, an average cycles per day, and a number cycles including a biological indicator; wherein the sterilization cycle table comprises a set of rows, each row corresponding to a single sterilization cycle performed by the first medical device processing component; and wherein the sterilization cycle visualization comprises one or more of a pie chart, a bar chart, or a graph.

Example 17

The method of any one or more of Examples 12 through 16, wherein the first medical device processing component comprises a biological indicator analyzer; wherein providing the set of device information comprises causing a device overview interface to display on the user device; wherein the device overview interface comprises two or more of: (i) a device identifier, (ii) a biological indicator analysis summary, (iii) an indicator well status, and (iv) an indicator analysis table.

Example 18

The method of Example 17, wherein the biological indicator analysis summary comprises a total number of analyses, a number of analyses per day, and a number of analyses indicating cycle success; wherein the indicator well status comprises a plurality of well indicators, each well descriptor comprising a vacancy indicator and an analyses duration indicator; and wherein the indicator analysis table comprises a set of rows, each row corresponding to a single biological indicator analysis performed by the indicator analyzer.

Example 19

A processing component network comprising: (a) a set of medical device processing components comprising: (i) a sterilizing cabinet, and (ii) a biological indicator analyzer; and (b) a means for configuring a network and monitoring medical device processing components; wherein the means for monitoring the set of medical device processing components is configured to: (i) connect to the set of medical device processing components, and (ii) display a set of device information generated by at least one device of the set of medical device processing components.

Example 20

The processing component network of Example 19, further comprising a means for providing communication between the set of medical device processing components IV. Explicit Definitions Further variations on, and features for, the inventors' technology will be immediately apparent to, and could be practiced without undue experimentation by, those of ordinary skill in the art in light of this disclosure. Accordingly, instead of limiting the protection accorded by this document, or by any document which is related to this document, to the material explicitly disclosed herein, the protection should be understood to be defined by the claims, if any, set forth herein or in the relevant related document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to such claims based on the above disclosure is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect.

When appearing in the claims, a statement that something is "based on" something else should be understood to mean that something is determined at least in part by the thing that it is indicated as being "based on." When something is required to be completely determined by a thing, it will be described as being "based exclusively on" the thing.

When used in the claims, "configured" should be understood to mean that the thing "configured" is adapted, designed or modified for a specific purpose. An example of "configuring" in the context of computers is to provide a computer with specific data (which may include instructions) which can be used in performing the specific acts the computer is being "configured" to do. For example, installing Microsoft® WORD on a computer "configures" that computer to function as a word processor, which it does by using the instructions for Microsoft WORD in combination with other inputs, such as an operating system, and various peripherals (e.g., a keyboard, monitor, etc.).

When used in the claims, "determining" should be understood to refer to generating, selecting, defining, calculating or otherwise specifying something. For example, to obtain an output as the result of analysis would be an example of "determining" that output. As a second example, to choose a response from a list of possible responses would be a method of "determining" a response. As a third example, to identify data received from an external source (e.g., a microphone) as being a thing would be an example of "determining" the thing.

When used in the claims, a "means for configuring a network and monitoring medical device processing components" should be understood as a limitation set forth in the form of a means for performing a specified function as provided for in the sixth paragraph of 35 U.S.C. § 112 in which the specified function is "configuring a network and monitoring medical device processing components" and the corresponding structure is a system having physical components such as servers, user devices, and communication hubs as shown in FIGS. 1, 4 and 5, where the components are programmed to provide interfaces that allow a user to configure devices, sites, and users, connect devices to a communication hub, and view and receive information and notifications generated by devices within the network (examples provided in FIGS. 10-12, 14-29, and the related discussion).

When used in the claims, a "means for providing communications between the set of medical device processing components" should be understood as a limitation set forth in the form of a means for performing a specified function as provided for in the sixth paragraph of 35 U.S.C. § 112 in which the specified function is "providing communications between the medical device processing components" and the corresponding structure is a system having physical components such as servers, user devices, and communication hubs as shown in FIGS. 1, 4 and 5, where the components are programmed to receive communications from an origin, determine their destination, prepare the communications for receipt by the destination, and provide the communications to at least the destination (examples provided in FIG. 13 and related discussion).

When used in the claims, a "set" should be understood to refer to a collection containing zero or more objects of the type that it refers to. So, for example, a "set of integers" describes an object configured to contain an integer value, which includes an object that contains multiple integer values, an object that contains only a single integer value, and an object that contains no integer value whatsoever.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A communication hub comprising:
(a) a processor;
(b) a memory configured to store instructions executable by the processor; and
(c) a network interface configured to place the communication hub in communication with a plurality of devices over a network;
wherein the processor is programmed to execute instructions to:
(i) receive a first set of device configurations from a user device,
(ii) create a device record for a first medical device processing component based upon the first set of device configurations,
(iii) establish a network connection to the first medical device processing component via the network interface,
(iv) provide a first set of device information to the user device, wherein the first set of device information is received from the first medical device processing component, and
(v) provide a task record to a second medical device processing component, wherein the task record describes a first task performed by the first medical device processing component, and wherein the first task is associated with sterilizing a medical device;
wherein the first set of device information is configured to cause the user device to display at least a portion of the first set of device information via a display of the user device, and
wherein the task record is required by the second medical device processing component in order to perform a second task associated with sterilizing the medical device.

2. The communication hub of claim 1, further comprising a housing that contains the processor, the memory, and the network interface.

3. The communication hub of claim 1, further comprising:
(a) a display; and
(b) a keyboard;
wherein the processor is programmed to execute instructions to cause the communication hub to:
(i) receive the first set of device configurations from the user device or the keyboard, and
(ii) display at least a portion of the first set of device information via the display of the communication hub.

4. The communication hub of claim 1, wherein the processor is programmed to execute instructions to:
(i) establish the network connection to a sterilization chamber as the first medical device processing component, and
(ii) provide the task record to a biological indicator analyzer as the second medical device processing component,
wherein the first task comprises a sterilization cycle performed in the sterilization chamber; and
wherein the second task comprises an analysis of a biological indicator used in the first task.

5. The communication hub of claim 1, wherein the processor is programmed to execute instructions to, when creating the device record:
   (i) determine a device identifier, a device model, and a device serial number based upon the first set of device configurations,
   (ii) associate the first medical device processing component with a site, wherein the site is associated with a geographic location, and
   (iii) associate a user with the site; and
   (iv) only provide the first set of device information to the user device when the user device is associated with the user that is associated with the site.

6. The communication hub of claim 1, wherein the processor is programmed to execute instructions to, when establishing the network connection to the first medical device processing component:
   (i) receive a device connection request from the user device,
   (ii) cause the user device to display a connection interface,
   (iii) receive a set of device connection information from the user device, the set of device connection information received via the connection interface, and
   (iv) attempt a connection to the first medical device processing component using the set of device connection information;
   wherein the connection interface comprises a description of connection instructions.

7. The communication hub of claim 1, wherein the processor is programmed to execute instructions to, when providing the first set of device information, cause the user device to display a device overview interface, wherein the device overview interfaces comprises two or more of:
   (i) a device identifier,
   (ii) a biological indicator analysis summary,
   (iii) an indicator well status, or
   (iv) an indicator analysis table.

8. A processing component network comprising:
   (a) a communication hub comprising:
      (i) a processor,
      (ii) a memory, and
      (iii) a network interface;
   (b) a sterilization chamber operable to perform a sterilization cycle on a medical device placed within the sterilization chamber; and
   (c) a biological indicator analyzer comprising an indicator well, the biological indicator analyzer operable to analyze a biological indicator placed in the indicator well;
   wherein the processor of the communication hub is programmed to execute instructions to:
      (i) receive a first set of device configurations,
      (ii) create a device record for the sterilization chamber based upon the first set of device configurations,
      (iii) establish a network connection to the sterilization chamber via the network interface based on the device record,
      (iv) receive a first set of device information from the sterilization chamber and provide the first set of device information to a user, wherein the first set of device information is configured to cause a user device to display at least a portion of the first set of device information via a display of the user device,
      (v) provide a task record to the biological indicator analyzer, wherein the task record describes a sterilization cycle performed by the sterilization chamber, and wherein the task record is required by the biological indicator analyzer to perform a biological indicator analysis.

9. A processing component network comprising:
   (a) a communication hub comprising:
      (i) a processor,
      (ii) a memory, and
      (iii) a network interface;
   (b) a set of medical device processing components operable to perform a sterilization process for a medical device, the set of medical device processing components comprising a first medical device processing component and a second medical device processing component, wherein each of the set of medical device processing components comprises a component processor and a component network interface; and
   (c) a user device comprising:
      (i) a user device processor,
      (ii) a user device memory, and
      (iii) a user device network interface;
   wherein the processor of the communication hub is programmed to execute instructions to cause the communication hub to:
      (i) receive a first set of device configurations from the user device,
      (ii) create a device record for the first medical device processing component based upon the first set of device configurations,
      (iii) establish a network connection to the first medical device processing component via the network interface,
      (iv) provide a first set of device information to the user device, wherein the first set of device information is received from the first medical device processing component, and
      (v) provide a task record to the second medical device processing component, wherein the task record describes a first task performed by the first medical device processing component;
   wherein the first set of device information is configured to cause the user device to display at least a portion of the first set of device information via a display of the user device, and
   wherein the task record is required by the second medical device processing component in order to perform a second task.

10. The processing component network of claim 9, wherein the first medical device processing component comprises a sterilization chamber;
   wherein the second medical device processing component comprises a biological indicator analyzer;
   wherein the first task comprises a sterilization cycle performed in the sterilization chamber; and
   wherein the second task comprises an analysis of a biological indicator used in the first task.

11. The processing component network of claim 9, wherein the network interface comprises a Wi-Fi transceiver;
   wherein the user device is selected from the group consisting of: a smartphone, a computer, a tablet, and a laptop;
   wherein the first set of device configurations comprises:
      (i) a site configuration,
      (ii) a device configuration, and
      (iii) a user configuration;
   wherein the first set of device information comprises five or more of:

(i) a cycle identifier
(ii) a device identifier,
(iii) a cycle status,
(iv) a biological indicator result,
(v) a number of total cycles,
(vi) a number of average cycles per day,
(vii) a number of cycles including a biological indicator,
(viii) a number of completed cycles,
(ix) a number of total indicator analyses,
(x) a number of indicator analyses per day,
(xi) a number of indicators having a pass result,
(xii) an indicator analyzer well status,
(xiii) a biological indicator identifier,
(xiv) a biological indicator lot number, and
(xv) a biological indicator color change.

12. The processing component network of claim 9, wherein the instructions to cause the communication hub to create a device record comprise instructions to:
   (i) determine a device identifier, a device model, and a device serial number based upon the first set of device configurations,
   (ii) associate the first medical device processing component with a site, wherein the site is associated with a geographic location, and
   (iii) associate a user with the site; and
   wherein the communication hub is further configured to only provide the first set of device information to the user device when the user device is associated with the user that is associated with the site.

13. The processing component network of claim 12, wherein the processor is further programmed to execute instructions to cause the communication hub to:
   (i) receive a notification from the first medical device processing component,
   (ii) determine a set of users that are associated with the site, the set of users including the user, and
   (iii) provide the notification to a set of user devices that are associated with the set of users.

14. The processing component network of claim 9, wherein the instructions to cause the communication hub to establish a network connection to the first medical device processing component comprise instructions to:
   (i) receive a device connection request from the user device,
   (ii) cause the user device to display a connection interface, wherein the connection interface is a graphical user interface,
   (iii) receive a set of device connection information from the user device, the set of device connection information received via the graphical user interface, and
   (iv) attempt a connection to the first medical device processing component using the set of device connection information;
   wherein the graphical user interface displays a set of connection instructions.

15. The processing component network of claim 14, wherein the connection interface is configured to receive, from the user device:
   (i) a network location identifier, a username, and a password, or
   (ii) a network pairing code comprising text usable by the communication hub to establish a network connection between the first medical device processing component and the communication hub.

16. The processing component network of claim 9, wherein the first medical device processing component comprises a sterilizing cabinet, and wherein the instructions to provide the first set of device information comprise instructions to provide a device overview interface to the user device, wherein the device overview interface comprises graphical display of two or more of:
   (i) a device identifier,
   (ii) a sterilization cycle summary,
   (iii) a sterilization cycle table, or
   (iv) a sterilization cycle visualization.

17. The processing component network of claim 16, wherein the sterilization cycle summary comprises display of a total number of cycles performed with the sterilizing cabinet, an average cycles performed with the sterilizing cabinet per day, and a number of cycles from the total number of cycles performed that included a biological indicator placed within the sterilizing cabinet during performance;
   wherein the sterilization cycle table comprises display of a set of rows, each row corresponding to a single sterilization cycle performed by the sterilizing cabinet; and
   wherein the sterilization cycle visualization comprises display of one or more of a pie chart, a bar chart, or a graph.

18. The processing component network of claim 9, wherein the first medical device processing component comprises a biological indicator analyzer, and wherein the instructions to provide the first set of device information comprise instructions to provide a device overview interface to the user device, wherein the device overview interface comprises two or more of:
   (i) a device identifier,
   (ii) a biological indicator analysis summary,
   (iii) an indicator well status, or
   (iv) an indicator analysis table.

19. The processing component network of claim 18, wherein the biological indicator analysis summary comprises descriptions of a total number of analyses, a number of analyses per day, and a number of analyses indicating cycle success;
   wherein the indicator well status comprises a plurality of well descriptors, each well descriptor comprising a vacancy indicator graphic and an analysis duration indicator graphic; and
   wherein the indicator analysis table comprises a set of rows, each row corresponding to a single biological indicator analysis performed by the biological indicator analyzer.

* * * * *